US011505579B2

(12) United States Patent
Leong et al.

(10) Patent No.: US 11,505,579 B2
(45) Date of Patent: Nov. 22, 2022

(54) METHODS OF TREATMENT AND RELATED COMPOSITIONS

(71) Applicant: ASCEND BIOPHARMACEUTICALS LTD, South Melbourne (AU)

(72) Inventors: Clement Leong, South Melbourne (AU); Geoffrey Pietersz, South Melbourne (AU)

(73) Assignee: ASCEND BIOPHARMACEUTICALS, INC., South Melbourne (AU)

( * ) Notice: Subject to any disclaimer, the term of this patent is extended or adjusted under 35 U.S.C. 154(b) by 0 days.

(21) Appl. No.: 17/430,171

(22) PCT Filed: Feb. 26, 2021

(86) PCT No.: PCT/AU2021/050167
§ 371 (c)(1),
(2) Date: Aug. 11, 2021

(87) PCT Pub. No.: WO2021/168516
PCT Pub. Date: Sep. 2, 2021

(65) Prior Publication Data
US 2022/0235097 A1    Jul. 28, 2022

(30) Foreign Application Priority Data

Feb. 28, 2020 (AU) ............................... 2020900586
Mar. 17, 2020 (AU) ............................... 2020900813

(51) Int. Cl.
| | |
|---|---|
| C07K 14/075 | (2006.01) |
| A61P 35/00 | (2006.01) |
| A61K 47/02 | (2006.01) |
| C07K 14/57 | (2006.01) |

(52) U.S. Cl.
CPC ............ *C07K 14/075* (2013.01); *A61K 47/02* (2013.01); *A61P 35/00* (2018.01); *C07K 14/57* (2013.01)

(58) Field of Classification Search
CPC ...... C07K 14/075; C07K 14/57; A61K 47/02; A61P 35/00
USPC ........................................................ 514/19.3
See application file for complete search history.

(56) References Cited

U.S. PATENT DOCUMENTS

2005/0201936 A1    9/2005  Wold et al.
2019/0389906 A1*  12/2019  Beswick ............... A61K 47/64

FOREIGN PATENT DOCUMENTS

WO    WO 2018/018073  *  2/2018  ............. C12N 15/00

OTHER PUBLICATIONS

Usme-Ciro et al., "Cytoplasmic RNA viruses as potential vehicles for the delivery of therapeutic small RNAs", (2013) Virology Journal 10, 185.
Wu et al., "Generation of a SMO homozygous knockout human embryonic stem cell line WAe001-A-16 by CRISPR/Cas9 editing", (2018) Stem Cell Research, 27:5-9.
Yoo et al., "RNAi-Mediated PD-L1 Inhibition for Pancreatic Cancer Immunotherapy," Sci. Rep., 9:4712, 9 pp. (2019).
Youn et al., "Modified mRNA as an alternative to plasmid DNA (pDNA) for transcript replacement and vaccination therapy," Expert Opinion on Biological Therapy, 15:1337-1348 (2015).
Accart et al., "Lymphocytic infiltration in the cutaneous lymphoma microenvironment after injection of TG1042", (2013) Journal of Translational Medicine, 11(226), 11 pp.
Amer, "Gene therapy for cancer: present status and future perspective", (2014) Molecular and Cellular Therapies 2, 27, 19 pp.
Cattaneo, "Paramyxovirus Entry and Targeted Vectors for Cancer Therapy", (2010) PLoS Pathogens 6(6), e10010973, 4 pp.
Chi et al., "Rab23 negatively regulates Gli1 transcriptional factor in a Su(Fu)-dependent manner", (2012) Cell Signal, 24(6):1222-1228.
Choi et al., "CRISPR-Cas9 disruption of PD-1 enhances activity of universal EGFRvIII CAR T cells in a preclinical model of human glioblastoma", (2019) J Immunother. Cancer, 7:304, 8 pages.
Clark et al., "Basal Cell Carcinoma: An Evidence-Based Treatment Update" American Journal of Clinical Dermatology, 15:197-216 (2014).
Clinical Trial NCT02550678 "A Study of the Efficacy and Safety of ASN-002 in Adult Patients With Low-risk Nodular Basal Cell Carcinoma (ASN-002-001)", First Posted Sep. 15, 2015, 8 pp.
ClinicalTrials.gov, Identifier NCT02690948 "Pembrolizumab With or Without Vismodegib in Treating Metastatic or Unresectable Basal Cell Skin Cancer", First Posted Feb. 24, 2016, 11 pp.
Cody et al., "Improving Oncolytic Herpes Simplex Virus for Metastatic Breast Cancer", (2013) Journal of Genetic Syndromes & Gene Therapy 4(1), 126, 2 pp.
Coon et al., "Molecular Therapy Targeting Sonic Hedgehog and Hepatocyte Growth Factor Signaling in a Mouse Model of Medulloblastoma," Molecular Cancer Therapy, 9:2627-2636 (2010).
Dahlen et al., "Bispecific antibodies in cancer immunotherapy", (2018) Ther. Adv. Vaccines Immunother., 6:3-17.
Diao et al., "Identi?cation of novel GLI1 target genes and regulatory circuits in human cancer cells", (2018) Molecular Oncology, 12:1718-1734.
Donnelly et al., "Sonic Hedgehog Mediates the Proliferation and Recruitment of Transformed Mesenchymal Stem Cells to the Stomach", (2013) PLOS One vol. 8, Issue. 9, Article. E75225, 11 pp.

(Continued)

*Primary Examiner* — Yan Xiao
(74) *Attorney, Agent, or Firm* — Fox Rothschild LLP

(57) ABSTRACT

The present invention relates to methods of treating a disease characterised by aberrant cell proliferation (e.g., a cancer) in a human subject in need thereof. In particular, the present invention relates to treating the above conditions by administering a therapeutically effective amount of at least one agent that increases activation of a receptor of at least one type II interferon and/or type I interferon, and administering to the subject at least one agent that inhibits the Hedgehog (Hh) signalling pathway (e.g., Vismodegib). Also provided are pharmaceutical compositions, including controlled release pharmaceutical compositions, containing at least one agent that increases activation of a receptor of at least one type II interferon and/or type I interferon (e.g., a checkpoint inhibitor), an inhibitor of Hh signalling pathway, and a controlled release matrix such as a $SiO_2$ matrix gel.

10 Claims, 1 Drawing Sheet

Specification includes a Sequence Listing.

(56) References Cited

OTHER PUBLICATIONS

Emeagi et al., "Lentiviral Vectors: A Versatile Tool to Fight Cancer," Current Molecular Medicine 13(4):602-625 (2013).
Filnke et al., "Recombinant Rhabdoviruses: Vectors for Vaccine Development and Gene Therapy," Current Topics in Microbiology and Immunology, 292:165-200 (2005).
Fukazawa et al., "Adenovirus-mediated cancer gene therapy and virotherapy (Review)," International Journal of Molecular Medicine, 25:3-10 (2010).
Gao et al., "Biology of AAV Serotype Vectors in Liver-Directed Gene Transfer to Nonhuman Primates," Gene Therapy, 13(22):1587-1594 (2006).
Guo et al., "Ectopic overexpression of second mitochondria-derived activator of caspases (Smac/DIABLO) or cotreatment with N-terminus of Smac/DIABLO peptide potentiates epothilone B derivative-(BMS 247550) and Apo-2L/TRAIL-induced apoptosis," Blood 99:3419-3426 (2002).
Hegde et al., "Novel therapy for therapy-resistant mantle cell lymphoma: Multipronged approach with targeting of hedgehog signaling," International Journal of Cancer, 131(12):2951-2960 (2012).
Hoang-Le et al., "A Kunjin replicon vector encoding granulocyte macrophage colony-stimulating factor for intra-tumoral gene therapy," Gene Therapy 16:190-199 (2009).
Hoffmann et al., "A platform for discovery of functional cell-penetrating peptides for efficient multi-cargo intracellular delivery", Scientific Reports, (2018) 8:12538 | DOI:10.1038/s41598-018-30790-2, 16 pp.
Hsiao et al., "Gli2 modulates cell cycle re-entry through autophagy-mediated regulation of the length of primary cilia", Journal of Cell Science (2018) 131, jcs221218. doi:10.1242/jcs.221218, 13 pp.
International Search Report dated May 4, 2021 for PCT/AU2021/050167, 6 pp.
International Second Written Opinion dated Aug. 10, 2021 for PCT/AU2021/050167, 7 pp.
Al-Tawfiq et al., "Vertebral osteomyelitis due to Aspergillus fumigatus in a patient with chronic granulomatous disease successfully treated with antifungal agents and interferon-gamma," Medical Mycology, 48:537-541 (May 2010).
Konermann et al., "Transcriptome Engineering with RNA-Targeting Type VI-D CRISPR Effectors," Cell, 173 (3):665-676 (2018).
Lacouture et al., "Characterization and Management of Hedgehog Pathway Inhibitor-Related Adverse Events in Patients With Advanced Basal Cell Carcinoma", (2018) The Oncologist, 21(10):1218-1229.
Laner-Plamberger et al., "Hedgehog/GLI Signaling Activates Suppressor of Cytokine Signaling 1 (SOCS1) in Epidermal and Neural Tumor Cells", (2013) PLoS One, 8(9):e75317, 13 pp.
Lear et al., "Basal Cell Carcinoma", (1997) Postgraduate Medical Journal, 73(863):538-542.
Li et al., "Peptide Blocking of PD-1/PD-L1 Interaction for Cancer Immunotherapy", (2018) Cancer Immunol. Res., 6: 178-188.
Li et al., "Novel-smoothened inhibitors for therapeutic targeting of naïve and drug-resistant hedgehog pathway-driven cancers", (2019) Acta Pharmacologica Sinica, 40(2):257-267.
Lu et al., "Sonic hedgehog antagonists induce cell death in acute myeloid leukemia cells with the presence of lipopolysaccharides, tumor necrosis factor—?, or interferons" Investigational New Drugs, 31:823-832 (2013).
Lundstrom, "Alphaviruses in Gene Therapy," Viruses, 7(5):2321-2333 (2015).
Masaru Katoh "Genomic testing, tumor microenvironment and targeted therapy of Hedgehog-related human cancers," Clinical Science, 133:953-970 (2019).
Merten et al., "Production of lentiviral vectors", (2016) Molecular Therapy—Methods & Clinical Development 3, 16017, 14 pp.
Morizono et al., "Lentiviral vector retargeting to P-glycoprotein on metastatic melanoma through intravenous injection," Nature Medicine, 11:346-352 (2005).
Munch et al., "DARPins: An Efficient Targeting Domain for Lentiviral Vectors", www.moleculartherapy.org, 19 (4):686-693 (Apr. 2011).
Munch et al. "Displaying High-affinity Ligands on Adeno-associated Viral Vectors Enables Tumor Cell-specific and Safe Gene Transfer," (2013) Molecular Therapy 21:109-118.
Nakamura, Masafumi et al. "Anti-patched-1 Antibodies Suppress Hedgehog Signaling Pathway and Pancreatic Cancer Proliferation", (2007) Anticancer Research, 27:3743-3748.
Narita et al., "GLI2 Knockdown Using an Antisense Oligonucleotide Induces Apoptosis and Chemosensitizes Cells to Paclitaxel in Androgen-Independent Prostate Cancer", (2008) Clinical Cancer Research, 14(18):5769-5777.
Nikanjam et al., "Advanced basal cell cancer: concise review of molecular characteristics and novel targeted and immune therapeutics", Annals of Oncology, 29(11):2192-2199 (2018).
Quetglas et al., "Alphavirus vectors for cancer therapy", (2010) Virus Research, 153(2):179-196.
Sasikumar et al., "A novel peptide therapeutic targeting PD1 immune checkpoint with equipotent antagonism of both ligands and a potential for better management of immune-related adverse events", (2013) J. Immunother. Cancer, 1: O24., 1 page.
Sasikumar et al., "A Rationally Designed Peptide Antagonist of the PD-1 Signaling Pathway as an Immunomodulatory Agent for Cancer Therapy", (2019) Cancer Therapy Mol. Cancer Ther., 18:1081-1091.
Sekulic et al., "Efficacy and Safety of Vismodegib in Advanced Basal-Cell Carcinoma", (2012) The New England Journal of Medicine, 366:2171-2179.
Singh et al., "Sonic Hedgehog Mutations Identified in Holoprosencephaly Patients Can Act in a Dominant Negative Manner," Human Genetics, 125(1):95-103 (2009).
Sofen et al., "A phase II, multicenter, open-label, 3-cohort trial evaluating the ef?cacy and safety of vismodegib in operable basal cell carcinoma", (2015) Journal of Academic Dermatology 73:99-105.
Stone et al., "Characterization of the human Suppressor of fused, a negative regulator of the zinc-?nger transcription factor Gli", (1999) Journal of Cell Science, 112, Pt(23):4437-4448.
Tang, "Inhibiting the Hedgehog Pathway in Patients with the Basal-Cell Nevus Syndrome", (2012) The New England Journal of Medicine, 366(23):2180-2188.
Trichas et al., "Use of the viral 2A peptide for bicistronic expression in transgenic mice", (2008) BMC Biology 6, 40, 13 pp.

\* cited by examiner

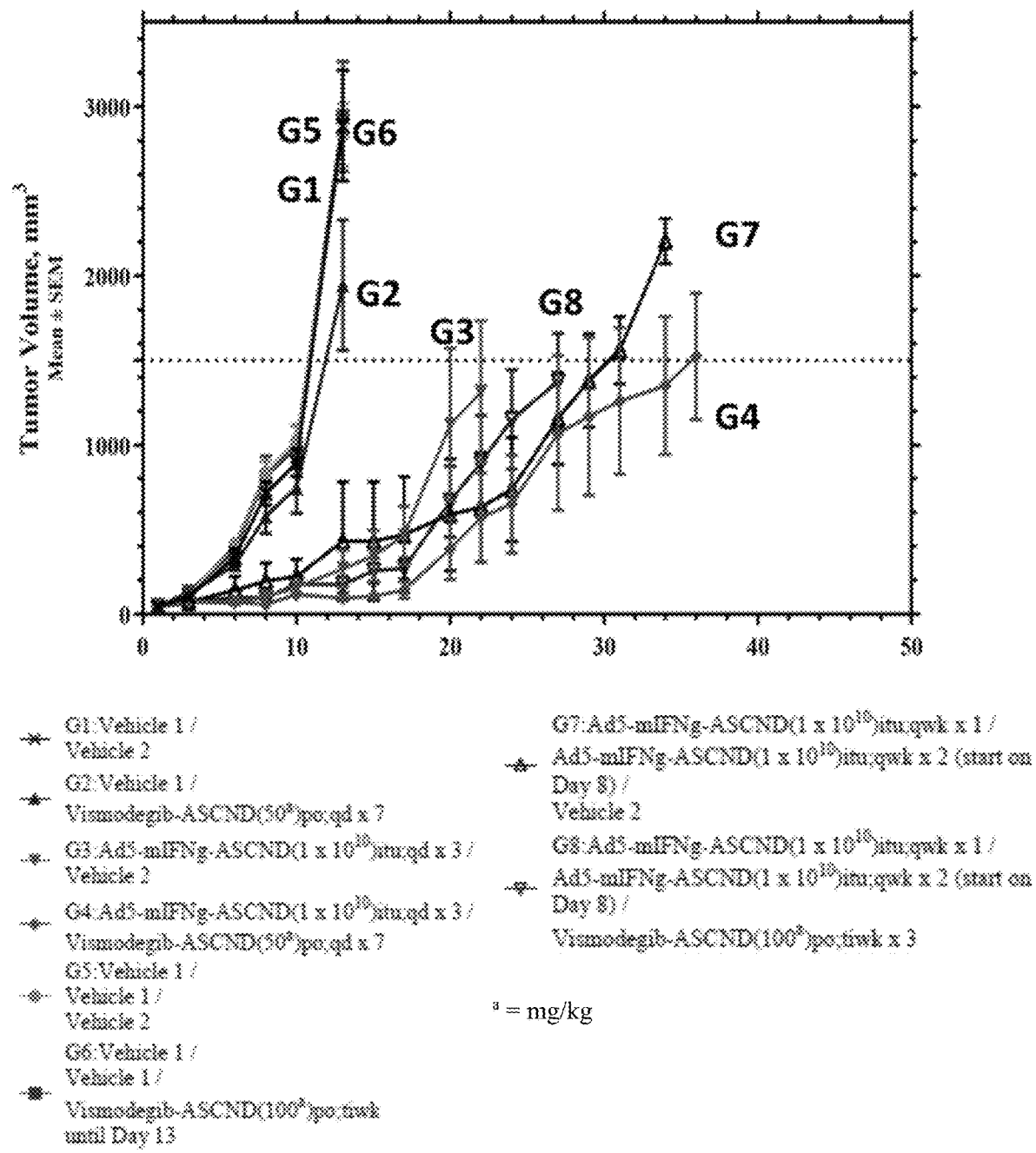

METHODS OF TREATMENT AND RELATED COMPOSITIONS

The present application is a U.S. National Stage Application under 35 U.S.C. § 371 of International Application No. PCT/AU2021/050167 filed Feb. 26, 2021, which claims the benefit of priority to Australian Patent Application No. 2020900586 filed Feb. 28, 2020 and Australian Patent Application No. 2020900813 filed Mar. 17, 2020, the disclosures of which are hereby incorporated by reference in their entireties.

FIELD OF THE INVENTION

The specification relates generally to the field of therapy for diseases characterised by aberrant cell proliferation.

BACKGROUND OF THE INVENTION

The effective treatment of conditions characterised by aberrant cell proliferation, e.g., cancers, remains an enormous challenge to clinicians. Inhibitors of the Hedgehog (Hh) signalling pathway, e.g., Vismodegib, have become a valuable addition to the arsenal of agents available for treating cancer and other proliferative disorders. Nevertheless, the development of resistance, or, more commonly, persistence in response to Hh signalling inhibitors diminishes their usefulness as a monotherapies. Further, the extended treatment generally required for treatment with Hh signalling inhibitors and their associated adverse effects on patients present further disadvantages for the use of Hh signalling inhibitors for treating proliferative disorders.

Thus, there is an ongoing need for therapeutic methods and compositions that can potentiate the therapeutic efficacy of inhibitors of the Hh signalling pathway.

SUMMARY OF THE INVENTION

The present inventors have surprisingly found that a combination of one or more inhibitors of the Hh signalling pathway (e.g., Vismodegib) in combination with an agent that increases activation of a receptor of at least one type II interferon and/or type I interferon synergistically induces a more complete elimination of aberrantly proliferating cells and reduces the required dosing level and treatment duration required for therapeutically effective use of inhibitors of the Hh signalling pathway.

Accordingly, provided herein is a method of treating a subject suffering from a disease characterised by aberrant cell proliferation, the method comprising administering to the subject a therapeutically effective amount of: (i) at least one agent that increases activation of a receptor of at least one type II interferon and/or type I interferon; and (ii) at least one agent that inhibits the Hedgehog (Hh) signalling pathway.

In some embodiments the subject to be treated is a mammal. In some preferred embodiments the subject to be treated is a human.

In some embodiments the at least one agent in (i) is a type II interferon and/or type I interferon, or a polynucleotide encoding a type II interferon and/or type I interferon, or an agonist for a receptor of at least one type II interferon and/or type I interferon.

In some embodiments the at least one agent in (i) comprises at least one type II interferon and/or type I interferon, or a polynucleotide encoding a type II interferon and/or type I interferon, or an agonist for a receptor of at least one type II interferon and/or type I interferon. In some embodiments the method includes administering a therapeutically effective amount of a type II interferon to the subject. In some embodiments, where a type II interferon is to be administered, the type II interferon is interferon gamma. In other embodiments the at least one agent in (i) is a polynucleotide for expression of a type II interferon and/or type I interferon in the subject to be treated. In some preferred embodiments, the polynucleotide is a polynucleotide for expression of interferon gamma.

In some preferred embodiments the polynucleotide for expression of the type II interferon and/or type I interferon is encoded by a recombinant virus administered to the subject. In some embodiments the recombinant virus is a recombinant DNA virus. In some embodiments the recombinant DNA virus is an adenovirus, an adeno-associated virus (AAV), a herpes simplex virus (HSV), or a lentivirus. In some preferred embodiments the recombinant DNA virus is an adenovirus. In some preferred embodiments the recombinant adenovirus is for expression of interferon gamma. In some preferred embodiments the adenovirus for expression of interferon gamma is ASN-002/SP-002. In some embodiments, where the method includes administering a recombinant virus for expression of the therapeutically effective amount of the type II interferon and/or a type I interferon, the recombinant virus is administered as at least $1\times10^8$ viral particles (vp) per lesion per dosing day.

In some embodiments the at least one agent in (i) is an agent that stimulates endogenous production and/or release of a type II interferon and/or type I interferon in the subject. In some embodiments the at least one agent in (i) is an agent that stimulates endogenous production and/or release of interferon gamma in the subject. In some embodiments the agent that stimulates endogenous production and/or release of a type II interferon and/or type I interferon includes one or more checkpoint inhibitors. In some embodiments the one or more checkpoint inhibitors inhibit activation of the PD-1 receptor, the CTLA-4 receptor, or both the PD-1 receptor and the CTLA-4 receptor.

In some preferred embodiments the one or more checkpoint inhibitors include a polypeptide checkpoint inhibitor or a peptide checkpoint inhibitor. In some embodiments the polypeptide checkpoint inhibitor or the peptide checkpoint inhibitor binds to a checkpoint receptor. In other embodiments the polypeptide checkpoint inhibitor or the peptide checkpoint inhibitor binds to a checkpoint receptor ligand. In some embodiments the polypeptide checkpoint inhibitor or the peptide checkpoint inhibitor binds to a checkpoint receptor ligand selected from the group consisting of: PD-L1, PD-L2, CD80/B7-1, CD86/B7-2, and any combination thereof. In some embodiments the polypeptide checkpoint inhibitor is an antibody or antigen-binding portion thereof. In some embodiments the antibody is is selected from the group consisting of: Ipilimumab, Pembrolizumab, Nivolumab, Atezolizumab, Avelumab, Durvalumab, Cemiplimab, AGEN1181, Tremelimumab, and any combination thereof. In some embodiments the antibody or antigen-binding portion thereof is bispecific. In some embodiments, where the antibody or antigen-binding portion thereof is bispecific, the bispecific antibody is selected from the group consisting of: M7824, MGD013, FS118, MCLA-134, XmAb-20717, ATOR-1015, and any combination thereof.

In some embodiments the one or more checkpoint inhibitors comprise a targeting polynucleotide. In some embodiments the the targeting polynucleotide is selected from the group consisting of: siRNA, RNAi, antisense oligonucleotides, CRISPR guide RNAs (gRNAs), and any combination thereof.

In some embodiments the at least one agent in (i) is administered systemically, intralesionally, or topically.

In some embodiments the at least one agent that inhibits the Hedgehog (Hh) signalling pathway inhibits the agent that inhibits the Hh signalling pathway inhibits a target selected from among SMO, PTCH1, GLI, SHHat, tGLI1, and SHH. In some embodiments the Hh signalling pathway target is SMO. In other embodiments the Hh signalling pathway target is SHH.

In some embodiments the agent that inhibits the Hh signalling pathway is a small molecule inhibitor. In some embodiments the small molecule inhibitor is selected from the group consisting of: Vismodegib, Sonidegib, Saridegib, IPI 926, LEQ-506, Taladegib, Itraconazole, Glasdegib, Jervine, CUR61414, BMS-833923, TAK-441, MRT-92, GDC-0449, HH-13, GANT61, and HH-20. In some preferred embodiments the small molecule inhibitor is Vismodegib. In some embodiments the small molecule inhibitor of the Hh signalling pathway is administered at a dose of about 150 mg to about 500 mg per day. In some embodiments the small molecule inhibitor of the Hh signalling pathway is administered at a dose of about 150 mg/day.

In other embodiments the agent that inhibits the Hh signalling pathway comprises a polypeptide, a polynucleotide, or a peptide.

In some embodiments the agent that inhibits the Hh signalling pathway comprises an antibody or an antigen-binding portion thereof that binds specifically to an Hh signalling pathway target. In some embodiments the agent comprises an antigen-binding portion against SHH, SMO, PTCH1, GLI, SHHat, or tGLI1. In some embodiments the agent comprises an antibody or an antigen-binding portion thereof against SHH. In some embodiments the antibody or antigen-binding portion thereof against SHH is an antibody or antigen-binding portion thereof selected from the group consisting of: 5E1, MEDI-5304, 1C11-2G4, antigen-binding portions thereof, and antibodies or antigen-binding portions thereof that compete with any one of 5E1, MEDI-5304, or 1C11-2G4 for binding to SHH. In other embodiments the agent comprises an antibody or an antigen-binding portion thereof against PTCH1. In some embodiments the antibody against PTCH1 is the α-PTCH1 antibody.

In some embodiments the agent that inhibits the Hh signalling pathway is a polynucleotide. In some embodiments the polynucleotide encodes a polypeptide that inhibits the Hh signalling pathway. In some embodiments, the polynucleotide is or encodes a miRNA, an siRNA, an RNAi, or a CRISPR gRNA, an antisense RNA, or an antisense oligonucleotide targeted against a Hh signalling pathway target.

In some embodiments, where the agent that inhibits the Hh signalling pathway is a polynucleotide, the subject is administered a recombinant virus for expression of the polynucleotide. In some preferred embodiments the recombinant virus is a recombinant DNA virus.

In some embodiments the agent that inhibits the Hh signalling pathway is administered systemically, intralesionally, or topically. In some embodiments the agent that inhibits the Hh signalling pathway is administered systemically. In other embodiments the agent that inhibits the Hh signalling pathway is administered intralesionally. In some embodiments, irrespective of route of administration, the agent that inhibits the Hh signalling pathway is administered as a controlled release formulation. In some embodiments, a controlled release formulation is administered through both intralesional and systemic routes.

In some embodiments administration of (i) at least one agent that increases activation of a receptor of at least one type II interferon and/or type I interferon; and (ii) the agent that inhibits the Hedgehog (Hh) signalling pathway are performed separately during a first dosing period.

In some embodiments, during the first dosing period, (ii) is administered after beginning administration of (i). In some embodiments, where (ii) is administered after beginning administration of (i), (ii) is administered at least one to three weeks after beginning administration of (i). In other embodiments during the first dosing period, (ii) is administered before administration of (i). In some embodiments (ii) is administered at least one to three weeks before beginning administration of (i).

In other embodiments (i) at least one agent that increases activation of a receptor of at least one type II interferon and/or type I interferon; and (ii) the agent that inhibits the Hedgehog (Hh) signalling pathway are co-administered during a first dosing period.

In some embodiments, (i) and (ii) are co-administered in a single formulation containing both (i) and (ii).

In some embodiments (i), (ii), or both (i) and (ii) are administered multiple times during a first dosing period.

In some embodiments (i) and (ii) are administered during a first dosing period and at least a second dosing period.

In some embodiments the subject is treated over a period of about one week to about twelve weeks. In some embodiments, where the subject is treated over a period of about one week to about twelve weeks, the dose of (ii) administered or treatment period with (ii) is limited to avoid induction of at least one adverse event associated with treatment with (ii).

In some embodiments the disease characterised by aberrant cell proliferation is selected from the group consisting of: a cancer, a fibrotic disease, or cutaneous warts. In some embodiments the disease characterised by aberrant cell proliferation is a cancer. In some embodiments the cancer is selected from the group consisting of: basal cell carcinoma, melanoma, lymphoma, squamous cell carcinoma, Merkel cell carcinoma, lung cancer, prostate cancer, sarcomas, medulloblastomas, cancers with desmoplastic stromas, colorectal cancer, ovarian cancer, breast cancer, gastric cancer, pancreatic cancer, mesothelioma, mesenchymal cancer, epithelial cancer, and adenocarcinomas. In some preferred embodiments the cancer to be treated is a basal cell carcinoma (BCC). In some embodiments the subject suffering from BCC suffers from Basal Cell Nevus Syndrome (BCNS) or sporadic BCC. In some embodiments, where the subject is to be treated for a cancer, the cancer is a recurrent cancer or a relapsing cancer.

In some embodiments at least two agents for inhibiting the Hh signalling pathway are administered. In some embodiments the at least two agents inhibit different Hh signalling pathway targets.

Furthermore, the present invention provides a method of treating a subject suffering from a disease characterised by aberrant cell proliferation, the method comprising administering to the subject a therapeutically effective amount of: (i) at least one checkpoint inhibitor; and (ii) at least one agent that inhibits the Hedgehog (Hh) signalling pathway.

In a further aspect provided herein is the use of at least one agent that increases activation of a receptor of at least one type II interferon and/or type I interferon for the manufacture of a medicament for the treatment of disease characterised by aberrant cell proliferation in a subject, wherein the subject has been or will be administered with at least one agent which inhibits Hedgehog (Hh) signalling pathway. In some embodiments the at least one agent that increases activation of the receptor comprises at least one type II interferon and/or type I interferon, a polynucleotide encoding a type II interferon and/or type I interferon.

In another aspect provided herein is the use of at least one least one agent which inhibits the Hedgehog (Hh) signalling pathway for the manufacture of a medicament for the treatment of a disease characterised by aberrant cell proliferation, in a subject, wherein the subject has been or will be administered with at least one agent that increases activation of a receptor of at least one type II interferon and/or type I interferon. In some embodiments the subject has been or will be administered at least one type II interferon and/or type I interferon, a polynucleotide encoding the type II interferon and/or type I interferon, or an agonist for a receptor of at least one type II interferon and/or type I interferon.

In another aspect provided herein is the use of at least one checkpoint inhibitor for the manufacture of a medicament for the treatment of disease characterised by aberrant cell proliferation in a subject, wherein the subject has been or will be administered with at least one agent which inhibits Hedgehog (Hh) signalling pathway.

In another aspect provided herein is the use of at least one least one agent which inhibits the Hedgehog (Hh) signalling pathway for the manufacture of a medicament for the treatment of a disease characterised by aberrant cell proliferation, in a subject, wherein the subject has been or will be administered with at least checkpoint inhibitor.

In a further aspect provided herein is a pharmaceutical composition for use in treatment of a disease characterised by aberrant cell proliferation, the pharmaceutical composition comprising: (i) at least one agent that increases activation of a receptor of at least one type II interferon and/or type I interferon; and (ii) at least one agent which inhibits the Hedgehog (Hh) signalling pathway. In some embodiments the pharmaceutical composition includes at least one type II interferon and/or type I interferon, or a polynucleotide encoding a type II interferon and/or type I interferon, or an agonist for a receptor of at least one type II interferon and/or type I interferon. In some embodiments the pharmaceutical composition comprises a recombinant virus comprising the polynucleotide encoding the type II interferon and/or type I interferon for expression in a subject. In some preferred embodiments of the pharmaceutical composition the interferon is interferon gamma.

In a related aspect provided herein is a pharmaceutical composition for use in treatment of a disease characterised by aberrant cell proliferation, where the pharmaceutical composition includes: (i) at least one checkpoint inhibitor; and (ii) at least one agent which inhibits the Hedgehog (Hh) signalling pathway.

In some embodiments of any of the above-mentioned pharmaceutical compositions, the pharmaceutical composition also includes a controlled release matrix, wherein each of (i) and (ii) are interspersed throughout the controlled release matrix. In some embodiments the controlled release matrix comprises a $SiO_2$ matrix gel. In some embodiments the $SiO_2$ matrix hydrogel comprises water and tetraethyl orthosilicate (TEOS) in a final molar ratio of between about 5:1 to about 4,000:1. In some embodiments the ratio of water to TEOS is about 400:1.

In some embodiments the pharmaceutical compositions are depot formulations.

The steps, features, integers, compositions and/or therapeutic agents disclosed herein or indicated in the specification of this application individually or collectively, and any combinations of two or more of said steps or features.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (e.g. one or more) of those steps, compositions of matter, groups of steps or group of compositions of matter.

The invention is hereinafter described by way of the following non-limiting Examples.

BRIEF DESCRIPTION OF THE ACCOMPANYING DRAWINGS

FIG. 1—Therapeutic response in B16F10 tumour-bearing mice to treatment monotherapy and combination treatment regimens with Vismodegib and Ad5-mIFNgamma. A line graph of tumour volume over a treatment period in treatment regimens G1-G8 as indicated. Mice administered both Vismodegib at 50 mg/kg daily for seven days and intralesional Ad5-mIFNgamma ($1\times10^{10}$ VPs/tumour) for three days (G4) exhibited the slowest tumour growth and highest viability at day 20.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in viral vector construction, transfection, gene knockdown, gene knockout, gene therapy, molecular genetics, cancer biology, cancer therapy, immunology, pharmacology, protein chemistry, and biochemistry).

Unless otherwise indicated, any recombinant molecular biology or immunological techniques described herein are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

The term "disease characterised by aberrant cell proliferation" as used herein, refers to any disease in which cell division is characterised by a diminished response, a lack of response, or an exaggerated response to one or more regulatory signals or proteins that modulate the rate of cell division, cell survival, and/or cell death in a particular population of cells. Examples of such regulatory signals include the regulatory signals or proteins include, but are not limited to, the presence or absence of a growth factor, checkpoint proteins, tumour suppressor proteins, pro-apoptotic proteins, and anti-apoptotic proteins. Examples of diseases characterised by aberrant cell proliferation include, but are not limited to, a cancer, a fibrotic disease, or cutaneous warts.

The term "type II interferon" as used herein, refers to interferons that bind to the interferon gamma receptor, e.g., interferon gamma. In an embodiment, the type II interferon is a human interferon. "type II interferon" also includes pegylated forms of type II interferon.

The term "type I interferon" as used herein, refers to a subclass of interferons that bind to and activate the interferon alpha receptor complex. Non-limiting examples of type I interferons include: interferon alpha, interferon beta, interferon epsilon, interferon kappa, and interferon omega 1. In an embodiment, the type I interferon is a human interferon. "type I interferon" also includes pegylated forms of type I interferon.

The term "agent that inhibits the Hedgehog (Hh) signalling pathway" as used herein, refers to any type of molecule that interferes with signal transduction upstream or downstream of the canonical receptor Patched (PTCH1) and/or the co-receptors growth arrest-specific gene 1 (GAS1), cell adhesion associated oncogene regulated (CDO/CDON), and Brother of CDO (BOC). Exemplary targets of inhibitors of Hh signalling pathway include, but are not limited to, Patch 1 (PTCH1), smoothened (SMO), glioma-associated oncogene homolog (GLI), SHH acetyl transferase (SHHat), truncated GLI1 (tGLI1), and sonic hedgehog (SHH). Inhibition of the activity of an Hh signalling pathway target by an inhibitor may be less than 100%, e.g., about 10% to about 95%, e.g., 20%, 30%, 40%, 50%, 60%, 70%, 80%, 90%, or another percent inhibition of the activity of a Hh signalling pathway target from about 10% to about 95%. An inhibitor of the Hh signalling pathway may be a small molecule (e.g., Sonidegib). Alternatively, the inhibitor may be a peptide, a protein, a nucleic acid, or a combination thereof, which can be administered directly in isolated form or indirectly via an expression vector (e.g., a plasmid or recombinant virus for expression of the encoded inhibitor in a human subject).

The term "agent that increases activation of a receptor of at least one type II interferon and/or type I interferon," as used herein, refers to any type of molecule that either directly or indirectly activate such receptors. Direct activators of such receptors include, but are not limited to, administered exogenous interferons, administered exogenous polynucleotides encoding interferons, administered peptides or peptidomimetic agonists, and small molecule agonists capable of activating a receptor of at least one type II interferon and/or type I interferon. Indirect activators of such receptors refer to those the administration of which result in increased production or secretion of an endogenous interferon capable of activating a receptor of at least one type II interferon and/or type I interferon. Such indirect activators include, but are not limited to, checkpoint inhibitors or combinations thereof that inhibit the activation of the PD-1 receptor, the CTLA-4 receptor, or both the PD-1 receptor and the CTLA-4 receptor.

The term "dosing period," as used herein, refers to a defined period of time over which at one or more doses of a first and a second therapeutic agent are administered to a subject in a desired temporal phase relationship. For example, within a first dosing period, a small molecule inhibitor may be administered twice at least 10 days before the beginning of administration of a recombinant virus expressing interferon gamma. Thus, within the first dosing period the small molecule inhibitor is administered before the recombinant virus. If a second dosing period commences, and the same sequence of administration is continued, the small molecule inhibitor is still considered to be administered before the recombinant virus even though it occurs after the previous administration of recombinant virus that occurred in the first dosing period.

The terms "effective amount" or "therapeutically effective amount," as used herein, refer to a sufficient amount of an administered agent (e.g., a recombinant virus, an inhibitor the Hh signalling pathway, or a purified protein) which will relieve to some extent one or more of the symptoms of the disease or condition being treated. The result can be reduction and/or alleviation of the signs, symptoms, or causes of a disease, or any other desired alteration of a biological system. A "therapeutically effective amount" of a therapeutic agent that is administered as part of a combination treatment can refer to an amount of the therapeutic agent that would be therapeutically effective when used on its own (i.e., as a monotherapy), or may refer to a reduced amount that is therapeutically effective by virtue of its combination with one or more additional therapeutic agents.

The term "recombinant virus," as used herein, refers to any virus that is genetically modified by experimental intervention and is capable of expressing a polynucleotide from an experimentally introduced expression cassette.

The term "administer" or "administered" as used herein, broadly encompasses exposing a subject to a therapeutic agent in question by direct or indirect means. In some cases, e.g., where a biotherapeutic agent such as a peptide, protein, or polynucleotide is to be administered, it can be delivered directly as an isolated purified reagent by any suitable route of administration, or, alternatively, it can be delivered indirectly by inducing expression of the biotherapeutic agent within the subject, e.g., by delivering to the human subject a plasmid DNA, modified mRNA, or a recombinant virus encoding the relevant biotherapeutic agent.

The term "adverse event" as used herein, refers to any undesirable clinical occurrence in a subject/patient (as compared to the subject's baseline health) and is any untoward medical occurrence defined as an unintended disease or injury or untoward clinical signs (including abnormal laboratory findings) in a patient. More specifically, grades of adverse events, as referred to herein, include those published under the "Common Terminology Criteria for Adverse Events" published by the U.S. National Cancer Institute (version 4.03 published 14 Jun. 2010). These include mild (grade 1) adverse events which present as mild symptoms not requiring medical intervention; moderate (grade 2) adverse events, which require minimal, local or noninvasive intervention; severe or medically significant (grade 3) adverse events, which are not immediately life-threatening, but may require hospitalization or prolongation of hospitalization; life-threatening (grade 4) adverse events requiring urgent intervention; and adverse event-related death (grade 5). Adverse events commonly associated with administration of agents for inhibiting the Hh signalling pathway for cancer therapy include, but are not limited to, myopathies, fatigue, alopecia (hair loss), dysgeusia (distortion of taste perception), weight loss, elevation of creatine phosphokinase, muscle cramps/spasms, and ovarian dysfunction, and new onset squamous cell carcinoma.

The terms "encoding" "encodes" "encoded" and the like as used herein, refer to any biomolecule for which a corresponding DNA or RNA sequence can be either transcribed into one or more RNAs or translated into one or more peptides or proteins. Examples of such encodable biomolecules include, but are not limited to, miRNAs, siRNAs, antisense RNAs, gRNAs, proteins, and peptides.

The term "expressing" or "expression" as used herein refers to the process of transcription and/or translation.

The term "purified" as used herein, in relation to a protein (e.g., "purified interferon gamma" and the like) refers to a protein provided in a form that is substantially free of contaminants normally associated with the protein in a native or natural environment.

The term "antibody" as used herein, includes polyclonal antibodies, monoclonal antibodies, bispecific antibodies, fusion diabodies, triabodies, heteroconjugate antibodies, chimeric antibodies including intact molecules as well as fragments thereof, and other antibody-like molecules. Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain.

The term "antigen-binding portion" as used herein, refers to a region on an antibody that binds to a specific antigen. Typically, such an antigen-binding portion will include at least a heavy chain variable domain ($V_L$) and a light chain variable domain ($V_H$), which together form the antigen-binding portion. An example of such an antigen-binding portion would include, e.g., single chain variable fragments (scFvs).

The term "small molecule" as used herein, refers to a chemical compounds or molecule having a molecular weight below 2000 daltons.

The terms "synergy" or "synergistic" as used herein refer to an effect (e.g., induction of cell death") resulting from the use of a combination of agents where the effect is quantitatively greater than the sum of the effects resulting from the use of each agent separately. For example, if agent "A" causes 30% cell death and agent "B" causes 30% cell death, the (non-synergistic) sum of such effects would be 60%. If, in fact, the combination of agents A and B results in greater than 60% cell death, their combined effect would be considered synergistic.

The terms "treating" or "treatment" as used herein, refer to both direct treatment of a subject by a medical professional (e.g., by administering a therapeutic agent to the subject), or indirect treatment, effected, by at least one party, (e.g., a medical doctor, a nurse, a pharmacist, or a pharmaceutical sales representative) by providing instructions, in any form, that (i) instruct a subject to self-treat according to a claimed method (e.g., self-administer a drug) or (ii) instruct a third party to treat a subject according to a claimed method. Also encompassed within the meaning of the term "treating" or "treatment" are prevention of relapse or reduction of the disease to be treated, e.g., by administering a therapeutic at a sufficiently early phase of disease to prevent or slow its progression.

Treatment of a Disease Characterised by Aberrant Cell Proliferation

The methods described herein relate to treating a human subject suffering from a disease characterised by aberrant cell proliferation, by administering a combination regimen of: (i) at least one agent that increases activation of a receptor of at least one type II interferon and/or type I interferon; and (ii) at least one agent that inhibits the Hedgehog (Hh) signalling pathway. Whilst not wishing to be bound by theory, inhibition of Hh pathway signalling in conjunction with increased type II and/or type I interferon receptor activity results in a synergistic anti-proliferative effect that will reduce treatment dosing and/or duration as compared to monotherapy.

In some embodiments the treatment methods described herein are performed on a mammalian subject such as a cow, sheep, horse, cat, mouse, rat, guinea pig, dog, pig, non-human primate, or a human. In some preferred embodiments the subject to be treated is a human subject.

Cancers that can be treated by any of the methods provided herein include, but are not limited to, basal cell carcinoma, melanoma, lymphoma, squamous cell carcinoma, Merkel cell carcinoma, lung cancer, prostate cancer, sarcomas, medulloblastomas, cancers with desmoplastic stromas, colorectal cancer, ovarian cancer, breast cancer, gastric cancer, pancreatic cancer, mesothelioma, mesenchymal cancer, epithelial cancer, and adenocarcinomas. In some preferred embodiments, the subject to be treated is suffering from basal cell carcinoma. In some embodiments, the subject suffering from basal cell carcinoma (BCC) suffers from Basal Cell Nevus Syndrome (BCNS) or sporadic BCC. In some embodiments the treatment methods are performed on a subject suffering from a recurrent cancer or relapsing cancer.

Fibrotic diseases that can be treated by the methods provided herein include, but are not limited to, Keloids, Scleroderma/systemic sclerosis, Nephrogenic systemic fibrosis, adhesive capsulitis, Dupuytren's contracture, and Arthrofibrosis.

In preferred embodiments, the dose of an agent that inhibits the Hedgehog (Hh) signalling pathway (e.g., Visomodegib), the dose of a (type II or type I) interferon (or agonist or checkpoint inhibitor), or both in a combination treatment may be reduced relative to a standard dose accepted in the art for administration of each agent alone. In some embodiments, of the treatment methods described herein a reduced dose avoids induction of at least one adverse event in the subject being treated. In some preferred embodiments, the dose to be administered is reduced by about 25% to about 95% relative to a standard dose, e.g., a 30%, 35%, 40%, 50%, 60%, 70%, 75%, 80%, 85%, 90%, or another percent dose reduction relative to a standard dose for the aberrant cell proliferation disease to be treated in a range of about 25% to about 95%. In some preferred embodiments, the dose is reduced by about 50% to about 85% relative to the a standard dose.

Symptoms, diagnostic tests, and prognostic tests for various types diseases characterised by aberrant cell proliferation are known in the art. See, e.g., the website of the National Comprehensive Cancer Network: (nccn.org/professionals/physician_gls/f_guidelines.asp), and British Medical Journal (BMJ) Best Practice (website at: bestpractice.bmj.com), respectively.

Inhibition of the Hedgehog Signalling Pathway

In some embodiments an agent that inhibits the Hh signalling pathway inhibits one or more Hh signalling pathway targets selected from the group consisting of: SMO, PTCH1, GLI, SHHat, tGLI1, SHH, and a combination thereof. The inhibitors to be administered can include, but are not limited to, small molecules, peptides, proteins, nucleic acids, or a combination thereof.

In some embodiments the agent is a small molecule inhibitor of the Hh signalling pathway. Suitable small molecule inhibitors of the Hh signalling pathway include, but are not limited to, Sonidegib/LDE225 (CAS 956697-53-3), Saridegib (CAS 1037210-93-7), Vismodegib (CAS 879085-55-9), LEQ-506 (CAS 1204975-42-7), Taledegib (CAS 1258861-20-9), Itraconazole (CAS 84625-61-6), Glasdegib (CAS 1095173-27-5), GANT61 (CAS 500579-04-4), Jervine (CAS 469-59-0), CUR61414 (CAS 334998-36-6), BMS-833923 (CAS 1059734-66-5), TAK-441 (CAS 1186231-83-3), MRT-92 (CAS 1428307-52-1), HH-13 (Li et al., 2019), GANT61 (CAS 500579-04-4), and HH-20 (Li et al., 2019). In some preferred embodiments the small molecule inhibitor to be administered is Vismodegib.

In some embodiments the agent that inhibits the Hh signalling pathway is a polypeptide. In some embodiments the polypeptide comprises an antibody or an antigen-binding portion thereof that binds specifically to an Hh signalling pathway target. In some embodiments the polypeptide comprises an antibody or an antigen-binding portion thereof against SHH, SMO, PTCH1, GLI, SHHat, or tGLI1. In some embodiments the polypeptide comprises an antibody or an antigen-binding portion thereof against SHH. Suitable examples of antibodies against SHH include, but are not limited to, 5E1, MEDI-5304, and antibodies that compete with any one of 5E1, MEDI 5304, or 1C11-2G4 for binding to SHH.

Suitable examples of antibodies against other Hh signalling pathway targets include, but are not limited to, α-Ptch1 against PTCH1 (Nakamura et al., 2007) and E5 against SMO (Santa Cruz Biotechnology, Cat No. sc-166685).

In some embodiments a polypeptide agent for inhibiting the Hh signalling pathway is a (non-antibody) negative regulator. In some embodiments the negative regulator is Rab 23 (Chi et al., 2012), human suppressor of fused hSu(fu) (Stone et al., 1999, or dominant negative SHH-G27A (Singh et al., 2009). In some embodiments the protein or peptide inhibitors are provided as conjugates or fusion proteins that include a cell penetrating peptide (CPP). CPPs are known in the art and commercially available (see, for example, Hoffmann et al., 2018). In some embodiments, where the inhibitor is a protein, the protein is an antibody inhibitor of the Hh signalling pathway. In some embodiments the inhibitor of the Hh signalling pathway includes a peptide. In some embodiments a peptide inhibitor comprises the amino acid sequence of HL2-m5 corresponding to SEQ ID NO:1:

(SEQ ID NO:1)
MDYKDDDDKGSGSTLSWO2beYEAMDMCTDT where O2beY corresponds to the unnatural amino acid O-(2-bromoethyl)-tyrosine (Owens et al., 2017).

In other embodiments the the agent that inhibits the Hh signalling pathway is a polynucleotide. In some embodiments the polynucleotide encodes any of the above-described polypeptides or peptides for inhibiting the Hh signalling pathway (e.g., an antibody against SHH).

In other embodiments, the polynucleotide acid does not encode a polypeptide that inhibits the Hh signalling pathway, but rather is or encodes a miRNA, an siRNA, an RNAi, or a CRISPR gRNA, an antisense RNA, or an antisense oligonucleotide targeted against a Hh signalling pathway target. The skilled person will appreciate that where a polynucleotide is utilised for expression of an RNA or protein, a suitable vector for expression of the RNA and/or protein in a mammalian subject can be administered to the subject to be treated either by in vivo transfection or by viral transduction using a recombinant virus as described herein.

In other embodiments the polynucleotide is an miRNA. Suitable miRNAs include, but are not limited to, miR-125b, miR-323, miR324-5p, miR-210, and miR-14. In other embodiments, the polynucleotide is an antisense RNA. Suitable antisense RNA inhibitors of the Hh signalling pathway include, but are not limited to, antisense oligomers against GLI1 (Hegde et al., 2012), GLI2 (Narita et al., 2008), and SMO (Gao et al., 2006). In other embodiments the polynucleotide to be administered comprises a gRNA for CRISPR targeting of the Hh signalling pathway. Suitable examples of gRNAs include, but are not limited to, gRNAs against GLI1 (Diao et al., 2018), GLI2 (Hsiao et al., 2018), and SMO (Wu et al., 2018). It will be appreciated by those skilled in the art that targeting gRNAs can be used for knock out or knock down of a target gene (Konermann et al., 2018) depending on the targeting enzyme (e.g., Cas9) used in conjunction with the gRNA.

In some embodiments, where the polynucleotide is to be administered by transient in vivo transfection, the polynucleotide is a chemically modified (coding or non-coding) RNA in which a proportion (e.g., 10%, 30%, 50%, or 100%) of at least one type of nucleotide, e.g., cytosine, is chemically modified to increase its stability in vivo. For example, in some cases modified cystosines are 5-methylcytosines. Such polynucleotides are particularly useful for delivery/transfection to cells in vivo, especially when combined with a transfection/delivery agent. In some cases, a chemically modified RNA is a chemically modified RNA in which a majority of (e.g., all) cystosines are 5-methylcytosines, and where a majority (e.g., all) of uracils are pseudouracils. The synthesis and use of such modified RNAs are described in, e.g., WO 2011/130624. Methods for in vivo transfection of DNA and RNA polynucleotides are known in the art as summarised in, e.g., Liu et al. (2015) and Youn et al. (2015).

Agents for Increasing Type II and/or Type I Interferon Receptor Activity

In some embodiments an agent to be administered for increasing Type II and/or Type I interferon receptor activity includes an exogenous interferon. In some embodiments of the treatment methods described herein, the amino acid sequence of the interferon to be administered comprises an amino acid sequence at least about 80% identical to the amino acid sequence of a human type II interferon, e.g., human interferon gamma (GenBank No. NP_000610.2), e.g., 82%, 85%, 88%, 90%, 92%, 95%, 97%, 99%, or another percent identical to the human interferon gamma sequence ranging from about 80% to 100% identical to the human interferon gamma sequence. In preferred embodiments the amino acid sequence of the interferon gamma to be administered is 100% identical to the amino acid sequence of human interferon gamma. In other embodiments the interferon gamma to be administered comprises an amino acid sequence at least about 80% identical to the amino acid sequence of a human type I human interferon, e.g., 82%, 85%, 88%, 90%, 92%, 95%, 97%, 99%, or another percent identical to the amino acid sequence of a human type I interferon. Suitable human type I interferons include one or more of: interferon alpha (GenBank No. AAA52724.1), interferon beta (GenBank No. AAC41702.1), interferon epsilon (GenBank No. AAQ88933), interferon kappa (GenBank No. EAW58563.1), and interferon omega 1 (GenBank No. CAA41626.1).

In some embodiments interferon gamma is administered as a substantially purified protein at level of purity considered to be safe for human administration, e.g., generally greater than 99% purity and about $5 \times 10^6$ IU/mg to about $4 \times 10^7$ IU/mg.

In other embodiments the type II or type I interferon to be administered is administered indirectly as a polynucleotide encoding a type II or type I interferon to be expressed in a human subject. In some preferred embodiments, the amino acid sequence of the encoded interferon is a type II interferon at least about 80% identical to the amino acid sequence of human interferon gamma (GenBank No. NP_000610.2), e.g., 82%, 85%, 88%, 90%, 92%, 95%, 97%, 99%, or another percent identical to the human interferon gamma sequence ranging from about 80% to 100% identical to the human interferon gamma sequence. In preferred embodiments the amino acid sequence of the encoded interferon gamma is 100% identical to the amino acid sequence of human interferon gamma.

In some preferred embodiments, where the type II or type I interferon is to be administered as a polynucleotide encoding the type II or type I interferon, the polynucleotide is administered via a recombinant virus for expression in a subject to be treated. In some embodiments, where recombinant virus is used for expression of the type II or type I interferon in a human subject, the same recombinant virus co-expresses an inhibitor of the Hh signalling pathway as described herein.

In some embodiments, where a type II interferon, a type I interferon is to be administered in the form of a polynucleotide as described herein, the polynucleotide is administered by transient in vivo transfection of a "naked" polynucleotide (e.g., a plasmid expression vector or an expression amplicon).

In some embodiments an agent for increasing type II and/or type I interferon receptor activity is an agent that stimulates endogenous production and/or release of a type II interferon and/or type I interferon in the subject. In some preferred embodiments the agent stimulates endogenous production and/or release of interferon gamma in the subject. In some embodiments the agent for increasing type II and/or type I interferon receptor activity includes one or more checkpoint inhibitors. In some embodiments the one or more checkpoint inhibitors inhibit activation of the PD-1 receptor, CTLA-receptor, or both. In some embodiments the agent comprises one or more checkpoint inhibitors that inhibit activation of the PD-1 receptor and inhibit activation of the CTLA-4 receptor.

In some embodiments the one or more checkpoint inhibitors include a polypeptide or a peptide. In some embodiments the checkpoint inhibitor polypeptide or the checkpoint inhibitor peptide bind to a checkpoint receptor. In other embodiments the checkpoint inhibitor polypeptide or the checkpoint inhibitor peptide bind to a checkpoint receptor ligand. In some embodiments, where the checkpoint inhibitor polypeptide or the checkpoint inhibitor peptide bind to a checkpoint receptor ligand, the checkpoint receptor ligand includes PD-L1, PD-L2, CD80/B7-1, CD86/B7-2, or any combination thereof.

In some embodiments, where the one or more checkpoint inhibitors include a polypeptide, the polypeptide is an antibody or antigen-binding portion thereof. Suitable checkpoint inhibitor antibodies include, but are not limited to, Ipilimumab, Pembrolizumab, Nivolumab, Atezolizumab, Avelumab, Durvalumab, Cemiplimab, AGEN1181, Tremelimumab, and any combination thereof. In some embodiments, where the one or more checkpoint inhibitors includes an antibody, the antibody is bispecific. Suitable bispecific antibodies include, but are not limited to, M7824 (see Clinical Trial Identifier NCT02699515), MGD013 (NCT03219268), FS118, MCLA-134, XmAb-20717, and ATOR-1015 (see, e.g., Dahlen et al., 2018).

In some embodiments the one or more checkpoint inhibitors include a peptide. Examples of suitable peptide checkpoint inhibitors include, but are not limited to, (D)PPA-1 (Chang et al., 2015), PL120131 (Boohaker et al., 2018), TPP-1 (Li et al., 2018), UNP-12 (Sasikumar et al., 2013), NP-12 (Saskikumar et al., 2019), and any combination thereof.

In other embodiments the one or more checkpoint inhibitors include a targeting polynucleotide. Suitable examples of targeting polynucleotides include siRNA, RNAi, antisense oligonucleotides, and any combination thereof. Such targeting polynucleotides may be directed against expression of one or more of, e.g., PD-1, PD-L1, PD-L2, CTLA4, CD80/B7-1, CD86/B7-2, or any combination thereof. Suitable targeting polynucleotides are known in the art, e.g., MN-siPDL1 (Yoo et al., 2019) and gRNA against PD-1 Choi et al. (2019).

Recombinant Viruses

In some embodiments, where (i) the at least one agent that inhibits the Hh signalling pathway and/or (ii) the at least one agent (e.g., a checkpoint inhibitor) that increases activation of a receptor of at least one type II interferon and/or type I interferon comprises a peptide, a polypeptide, or a polynucleotide, a recombinant virus is administered to induce expression of the peptide, polypeptide, or polynucleotide when administered to the subject (e.g., a human subject). A variety of recombinant virus types are suitable for expression of a type II or type I interferon and, optionally, a polypeptide, a polynucleotide, or a peptide that inhibits the Hh signalling pathway as described herein.

In some embodiments, the recombinant virus to be administered is a DNA virus. Suitable types of DNA viruses include adenovirus, adeno-associated virus (AAV), herpes simplex virus (HSV), retrovirus, and lentivirus. Methods for design, production, and use of such types of recombinant DNA viruses are established in the art, as exemplified in Fukazawa et al. (2010) and in "Gene Therapy Protocols" for adenovirus; "Adeno-Associated Virus: Methods and Protocols" for AAV; Cody et al. (2013) and "Herpes Simplex Virus: Methods and Protocols" for HSV; "Gene Therapy Protocols Vol. 1: Production and In Vivo Applications of Gene Transfer Vectors" and Amer et al. (2014) for retrovirus; and Merten et al. (2016) and Emeagi et al. (2013) for lentivirus. In some preferred embodiments, the recombinant virus to be used in the treatment method is an adenovirus. In some preferred embodiments the recombinant adenovirus is ASN-002, a replication-deficient type 5 adenovirus for expression of interferon gamma (also known as Tg1042 and SP-002) (Urosevic, 2007; Liu et al., 2004; Dummer et al., 2004 and 2010; Accart et al., 2013; Khammari et al., 2015; Dreno et al., 2014; Hillman et al., 2004).

In other embodiments, the recombinant virus to be administered is a recombinant, replication-deficient or replication-competent RNA virus. Suitable types of replication deficient or replication-competent RNA viruses Alphavirus (e.g., Sindbis or Semliki Forest Virus), Flavivirus (e.g., Kunjin virus), Paramyxovirus (e.g., Sendai virus), Rhabdovirus (e.g., vesicular stomatitis virus), and Orthomyxovirus (e.g., influenza A virus). Methods for design, production, and use of such types of recombinant RNA viruses are established in the art, as exemplified in Lundstrom (2015) and Quetglas et al. (2010) for Alphavirus; Hoang-Le et al. (2009) and Usme-Ciro et al. (2013) for Flavivirus; Cattaneo (2010) for Paramyxovirus; Finke et al. (2005) and Chang et al. (2010) for Rhabdovirus; and U.S. Pat. No. 8,475,806 for Orthomyxovirus.

In some embodiments, the recombinant DNA or RNA virus is a replication deficient virus incapable of replication in transduced cells. In other embodiments, the recombinant virus is a replication-competent virus, which can replicate in a transduced host cell. Alternatively, the recombinant virus is a conditionally replication-competent virus that can replicate only in particular cell types or in cells with a particular expression profile, e.g., p53-deficient cancer cells.

Examples of suitable promoters for driving expression of biotherapeutic agents from a recombinant virus in a method described herein include, but are not limited to, constitutive promoters such as, CMV, CAG, EF-1-I, HSV1-TK, SV40, β-actin, and PGK promoters. In other embodiments, a promoter is an inducible promoters, such as those containing TET-operator elements. In certain embodiments, target-selective promoters are used to drive expression of biotherapeutic agents in specific cell types or specifically in cells exhibiting aberrant cell proliferation. Examples of suitable promoters useful for the methods described herein include, but are not limited to, the erb 2 promoter (breast cancer), the carcinoembryonic antigen promoter (colorectal cancer), the urokinase-type plasminogen activator receptor promoter (colorectal cancer), the tyrosinase promoter (melanoma), the melacortin receptor (melanoma); the human telomerase reverse transcriptase (hTERT) promoter (multiple cancers), the RAS-related nuclear protein promoter (multiple cancers), the breast cancer metastasis suppressor 1 promoter (multiple cancers), the Rad51C promoter (multiple cancers), and the minichromosome maintenance complex component 5 promoter (multiple cancers).

In some embodiments, where two or more proteins are to be expressed from a recombinant virus, the recombinant virus contains an expression cassette encoding a polycistronic mRNA (a "polycistronic expression cassette"), which, upon translation gives rise to independent polypeptides comprising different amino acid sequences or functionalities, e.g., interferon gamma and a protein inhibitor of the Hh signalling pathway (e.g., hSu(fu)). In some embodiments, a polycistronic expression cassette encodes a "polyprotein" comprising multiple polypeptide sequences that are separated by encoded by a picornavirus, e.g., a foot-and-mouth disease virus (FMDV) viral 2A peptide sequence. The 2A peptide sequence acts co-translationally, by preventing the formation of a normal peptide bond between the conserved glycine and last proline, resulting in ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. which during translation allow cleavage of the nascent polypeptide sequence into separate polypeptides. See, e.g., Trichas et al. (2008).

In other embodiments, a polycistronic expression cassette may incorporate one or more internal ribosomal entry site (IRES) sequences between open reading frames incorporated into the polycistronic expression cassette. IRES sequences and their use are known in the art as exemplified in, e.g., Martinez-Sales (1999).

In some embodiments, a recombinant virus used in the method has targeted tropism, e.g., tropism for a particular cell type as reviewed in Bucholz et al. (2015). Suitable targeting moieties, to be incorporated into a recombinant viral capsid surface, include ligands that bind to cell surface receptors that are overexpressed by overproliferating cells (e.g., cancer cells). For example, the Her2/neu receptor, frequently overexpressed in breast cancer cells, can be targeted by incorporating a designed ankryrin repeat protein (DARPin) ligand, as has been done for lentivirus (Münch et al. 2011) in AAV (Münch et al. 2013). In another example a recombinant lentivirus is designed to target P-glycoprotein, overexpressed on the surface of melanoma cells, by incorporating an antibody into the viral capsid surface (Morizono et al. 2005).

Dosing Regimens

The person of ordinary skill in the art will appreciate that a suitable therapeutically effective dose of an agent that inhibits the Hh signalling pathway when administered in combination with an agent that increases activation of a receptor of at least one type II interferon and/or type I interferon, as described herein, will depend upon factors such as the particular Hh signalling pathway inhibitor, the development of adverse effects of the treatment, the particular agent, the disease stage, the characteristics of the subject or host in need of treatment (e.g., weight), the properties of the particular type of disease to be treated, the proposed route of administration, etc., but can nevertheless be determined in a manner known in the art. The desired dose may conveniently be presented in a single dose or as divided doses administered simultaneously (or over a short period of time) or at appropriate intervals, for example as two, three, four or more sub-doses per day.

In general, agents being administered in combination do not necessarily have to be administered in the same pharmaceutical composition, and may, because of different physical and chemical characteristics, be administered by different routes.

The time period between the multiple administration steps may range from, a few minutes to several days, depending upon the properties of each pharmaceutical agent, such as potency, solubility, bioavailability, plasma half-life and kinetic profile of the pharmaceutical agent. Circadian variation of various physiological parameters may also be evaluated to determine the optimal dose interval.

Initial administration can be via any route practical, such as, for example, an intravenous injection, a bolus injection, infusion over 5 minutes to about 5 hours, a pill, a capsule, topical application, transdermal patch, and the like, or combination thereof. In some embodiments, administration is by sub-cutaneously, such as intralesional injection perilesional injection, or injection in close proximity to a lesion (for example with about 5 cm or within about 1 cm). In some embodiments a Hh signalling pathway inhibitor is administered orally, and the type II or type I interferon (e.g., by way of a recombinant virus) is administered intralesionally.

In some embodiments of the treatment methods described herein either of: (i) at least one agent that increases activation of a receptor of at least one type II interferon and/or type I interferon; or (ii) at least one agent that inhibits the Hedgehog (Hh) signalling pathway is administered systemically, intralesionally, or topically.

In some preferred embodiments, e.g., where the subject to be treated presents with lesions/tumours amenable to direct local administration (e.g., basal cell carcinoma), administration of (i) is intralesional. In some embodiments, administration of (i) is intralesional and administration of (ii) is systemic.

In some embodiments administration of each of (i) and (ii) is performed separately during a first dosing period, i.e., a period over which a first set of doses of (i) and (ii) are administered to the subject. In some embodiments, during the first dosing period, (ii) is administered after beginning dosing with (i). In some embodiments (ii) is administered at least one day to about eight weeks after beginning administration of (i), e.g., one day, two days, three days, four days, five days, six days, one week, two weeks, three weeks, four weeks, six weeks, seven weeks, or another period from at least one day to about eight weeks after beginning administration of (i). In some embodiments (ii) is administered at least one to three weeks after beginning administration of (i).

In other embodiments, during the first dosing period (ii) is administered before administration of (i). In some embodiments (ii) is administered at least one day to about eight weeks before beginning administration of (i), e.g., one day, two days, three days, four days, five days, six days, one week, two weeks, three weeks, four weeks, six weeks, seven weeks, or another period from at least one day to about eight weeks before beginning administration of (i). In some preferred embodiments (ii) is administered about 10 days to about 14 days before beginning administration of (i).

In some embodiments (i) and (ii) are co-administered during a first dosing period, i.e., they are administered to the subject within less than one day of each other. In some embodiments co-administration of (i) and (ii) includes administration of (i) and (ii) within about 1 minute to about 22 hours of each other within a first dosing period, e.g., 5 minutes, 30 minutes, 1 hours, 2 hours, 8 hours, 12 hours, 18, hours or another time interval from about 1 minute to about 22 hours during a first dosing period. In some embodiments, where (i) and (ii) are co-administered, they are co-administered in a single formulation containing both (i) and (ii).

In some embodiments (i), (ii), or both (i) and (ii) are administered multiple times during a first dosing period. In some embodiments (i), (ii), or both (i) and (ii) are administered at a frequency of between about once per week to about once per day during a first dosing period, e.g., once per five days, once per four days, once per three days, once per two days, or another frequency from about once per week to about once per day. In some embodiments, where (i) and (ii) are administered multiple times during a first dosing period, the dosing frequency for (ii) is lower than that for (i). In other embodiments the dosing frequency for (i) is lower than that for (ii). In some embodiments the dosing frequency for (i) and (ii) is the same.

In some embodiments, a subject to be treated is administered a combination treatment as described herein over multiple dosing periods including at least first and second dosing periods. The number of dosing periods may range from 1 to 14, e.g., 2, 3, 4, 5, 6, 8, 10, 12, or another number of dosing periods from 1 to 14. In some embodiments the treatment includes at least first and second dosing periods. Where a subject is treated over multiple dosing periods, the total aggregate dose (i) and/or (ii) may be varied among different dosing periods.

Monotherapy for cell proliferation diseases (e.g., cancer) with agents that inhibit the Hh signalling pathway for treatment of a disease are generally acknowledged to cause adverse events especially in view of the duration (usually about 10 months) and dose of these agents required for an effective response. However, such adverse effects (e.g., muscle cramps/spasms, fatigue, and myopathies) commonly result in patients stopping treatment with such agents before a full course of treatment has been completed. Indeed, adverse events (e.g., muscle spasms) often begin as early as two months into the treatment (Lacouture et al, 2018). In contrast, in the combination treatment methods described herein, synergy between treatment with (i) at least one agent that increases activation of a receptor of at least one type II interferon and/or type I interferon; and (ii) agent that inhibits the Hedgehog (Hh) signalling pathway affords a substantially reduced duration and/or dose of (ii). Thus, in some embodiments the dose of (ii) administered or treatment period with (ii) in combination with (i) is limited to avoid induction of at least one adverse event associated with treatment with (ii) alone. Accordingly, in some embodiments the dose of (ii) administered in a combination treatment with (i) as described herein is about 10% to about 90% less than a dose of (ii) required for monotherapy with (ii) while at the same time avoiding induction of more than a moderate event associated with monotherapy treatment with (ii), e.g., 20% less, 30% less, 40%, less, 50% less, 60% less, 70% less, 80% less, or another value from about 10% to about 90% less than a dose of (ii) required for monotherapy with (ii) while avoiding induction of more than a moderate event associated with monotherapy treatment with (ii). In other embodiments the duration of the treatment period with (ii) administered in a combination treatment with (i) as described herein is about 10% to about 90% less time than the duration of the treatment with (ii) required for monotherapy with (ii) while at the same time avoiding induction of more than a moderate event associated with monotherapy treatment with (ii), e.g., 20% less, 30% less, 40%, less, 50% less, 60% less, 70% less, 80% less, or another value from about 10% to about 90% less time than the duration of the treatment period with (ii) required for monotherapy with (ii) while avoiding induction of more than a moderate event associated with monotherapy treatment with (ii).

In some embodiments, where the subject to be treated is suffering from basal cell carcinoma, the a dosing period comprises 2-3 administrations of (i) in a single week and daily administration of (ii). In other embodiments, where the subject to be treated is suffering from basal cell carcinoma, a dosing period comprise 2-3 administrations in two weeks.

In some embodiments a treatment duration, which includes all dosing periods, is from about 3 weeks to about 40 weeks, e.g., 4 weeks, 5 weeks, 8 weeks, 12 weeks, 16 weeks, 18 weeks, 20 weeks, 24 weeks, 30 weeks, 32 weeks, 34 weeks, 36 weeks, or another treatment duration from about 3 weeks to about 40 weeks.

In some embodiments, administration of a recombinant virus for expression of a type II and/or type I interferon and, optionally, expression of an inhibitor of the Hh signalling pathway inhibitor, is by an intralesional route of administration. In some embodiments, where a polypeptide (e.g., an antibody) or polynucleotide (e.g., shRNA) to inhibit the Hh signalling pathway is to be expressed from a recombinant virus, it is co-expressed with a type II or type I interferon from the same recombinant virus. In other embodiments, where a polypeptide (e.g., an antibody) or polynucleotide (e.g., shRNA) to inhibit the Hh signalling pathway is to be expressed in a subject by administering a recombinant virus, it is expressed from a recombinant virus that is separate and distinct from the recombinant expression virus used to drive expression of a type II or type I interferon in a human subject.

In some embodiments, the administered intralesional total dose of recombinant virus is from about $1 \times 10^7$ viral particles/lesion to about $1 \times 10^{12}$ viral particles/lesion, e.g., $2 \times 10^7$, $3 \times 10^7$, $4 \times 10^7$, $5 \times 10^7$, $6 \times 10^7$, $8 \times 10^7$, $1 \times 10^8$, $1.5 \times 10^8$, $2 \times 10^8$, $3 \times 10^8$, $4 \times 10^8$, $6 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $8 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $8 \times 10^{11}$, $9 \times 10^{11}$, or another number of viral particles/lesion from about $1 \times 10^7$ viral particles/lesion to about $1 \times 10^{12}$ viral particles/lesion. In some embodiments, the intralesional viral dose ranges from about $2 \times 10^{10}$ viral particles/lesion to about $3 \times 10^{11}$ viral particles/lesion. In some embodiments the recombinant virus for expression of the therapeutically effective amount of the type II interferon and/or a type I interferon is administered as at least $5 \times 10^7$ viral particles to about $5 \times 10^9$ viral particles per lesion per dosing day. In some preferred embodiments the recombinant virus for expression of the therapeutically effective amount of the type II interferon and/or a type I interferon is administered as at least $1 \times 10^8$ viral particles to about $1 \times 10^9$ viral particles per lesion per dosing day. In some preferred embodiments the recombinant virus for expression of the therapeutically effective amount of the type II interferon and/or a type I interferon is administered as at least $1 \times 10^9$ viral particles per lesion per dosing day.

In some embodiments, the subject to be treated is administered multiple doses of a recombinant virus expressing a Type I or Type II interferon in a combination treatment with a small molecule inhibitor of the Hh signalling pathway in each dosing period.

In other embodiments, where administration of the recombinant virus is intralesional, the total aggregate dose of recombinant viral particles per dosing period ranges from about $1 \times 10^8$ viral particles/lesion to about $1 \times 10^{13}$ viral particles/lesion, e.g., $2 \times 10^8$, $3 \times 10^8$, $4 \times 10^8$, $5 \times 10^8$, $6 \times 10^8$, $8 \times 10^8$, $1 \times 10^9$, $1.5 \times 10^9$, $2 \times 10^9$, $3 \times 10^9$, $4 \times 10^9$, $6 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, $4 \times 10^{12}$, $5 \times 10^{12}$, $6 \times 10^{12}$, $8 \times 10^{12}$, $9 \times 10^{12}$ or another number of total viral particles per dosing period from about $1 \times 10^8$ viral particles/lesion to about $1 \times 10^{13}$ viral particles/lesion.

In some embodiments, where administration of the recombinant virus is by systemic, intraperitoneal, or intrapleural administration, the total aggregate viral dose per dosing period for a recombinant virus is about $1 \times 10^9$ viral particles to about $1 \times 10^{14}$ viral particles per dosing period, e.g., $2 \times 10^9$, $3 \times 10^9$, $4 \times 10^9$, $5 \times 10^9$, $6 \times 10^9$, $8 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $9 \times 10^{10}$, $1 \times 10^{11}$, $1.5 \times 10^{11}$, $2 \times 10^{11}$, $3 \times 10^{11}$, $4 \times 10^{11}$, $6 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $8 \times 10^{13}$, $9 \times 10^{13}$ or another number of total viral particles per dosing period from about $1 \times 10^9$ viral particles to about $1 \times 10^{14}$ viral particles.

In some embodiments, where the agent that inhibits the Hh signalling pathway is a small molecule inhibitor (e.g., Vismodegib), and administration is intralesional, the dose concentration is at least about 5 µM to about 40 µM per lesion, e.g., 10 µM, 15 µM, 20 µM, 25 µM, 30 µM, 35 µM per lesion, or another dose concentration from about 5 µM to about 40 µM. In some embodiments, the dose concentration is at least about 20 µM to about 100 µM per lesion, e.g., 25 µM, 30 µM, 45 µM, 50 µM, 60 µM, 70 µM, 80 µM, 90 µM, or another concentration per lesion from about 20 µM to about 100 µM. In other embodiments the intralesional dose of the small molecule inhibitor (e.g., Vismodegib) ranges from about 0.02 mg/lesion to about 10 mg/lesion per administration, e.g., about 0.05 mg/lesion, 0.075 mg/lesion, 0.1 mg/lesion, 0.15 mg/lesion, 0.2 mg/lesion, 0.25 mg/lesion, 0.3 mg/lesion, 0.5 mg/lesion, 0.7 mg/lesion, 0.8 mg/lesion, 1 mg/lesion, 1.5 mg/lesion, 2 mg/lesion, 3 mg/lesion, 3.5 mg/lesion, 4 mg/lesion, 4.5 mg/lesion, 5 mg/lesion, 5.5 mg/lesion, 6 mg/lesion, 7 mg/lesion, 8 mg/lesion, 9 mg/lesion or another intralesional dose from about 0.02 mg/lesion to about 10 mg/lesion per administration. In some preferred embodiments, the intralesional dose of a small molecule Hh signalling pathway inhibitor ranges from about 2.5 mg/lesion to about 10 mg/lesion.

In some embodiments, a disease to be treated, as described herein, includes treatment by systemic administration of one or more inhibitors as described in the combination treatment methods provided herein. In other embodiments, the administration is intraperitoneal administration. In some embodiments, the administration is intrapleural administration.

In some embodiments, where the agent that inhibits the Hh signalling pathway is a small molecule inhibitor (e.g., Vismodegib), and administration is systemic, the dose concentration in circulation is about 10 µM to about 80 µM, e.g., 15 µM, 20 µM, 25 µM, 30 µM, 35 µM, 40 µM, 45 µM, 50 µM, 60 µM, 70 µM, or another concentration in circulation from about 10 µM to about 80 µM. In some preferred embodiments, the dose concentration in circulation is at least about 20 µM to about 40 µM, e.g., 25 µM, 30 µM, 35 µM, or another concentration in circulation from at least about 20 µM to about 40 µM. In some embodiments, where the one or more inhibitors is administered by systemic, intraperitoneal, or intrapleural administration, each administered dose is in a range of about 0.1 mg/kg to about 12 mg/kg per administration, e.g., 0.20 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 10 mg/kg, or another dose ranging from about 0.1 mg/kg to about 12 mg/kg. In some preferred embodiments, the dose of the one or more inhibitors is about 2 mg/kg to about 5 mg/kg.

In some embodiments the small molecule inhibitor of the Hh signalling pathway is administered at a dose of about 50 mg to about 500 mg per dosing day, e.g., 75 mg, 100 mg, 150 mg, 200 mg, 300 mg, 400 mg, 450 mg, or another total dose of about 50 mg to about 500 mg per dosing day. In some embodiments the small molecule inhibitor of the Hh signalling pathway is administered at a total dose of about 150 mg per dosing day.

In other embodiments, treatment of a disease, as described herein (e.g., a skin cancer), includes topical administration of an inhibitor as descried herein. In some embodiments, an inhibitor is administered topically as a formulation ranging from about 0.01% (w/v) to about 3% (w/v), e.g., 0.02%, 0.03%, 0.04%, 0.05%, 0.08%, 0.1%, 0.2%, 0.3%, 0.4%, 0.5%, 0.6%, 0.7%, 0.8%, 1%, 1.2%, 1.3%, 1.5%, 1.7%, 2%, 2.2%, 2.5%, 2.8%, or another topical concentration from about 0.01% (w/v) to about 3% (w/v). In some embodiments, the inhibitor concentration is about 0.02% (w/v) to about 2%. In preferred embodiments the topical concentration is about 0.1% to about 0.5%.

In some embodiments, the subject to be treated receives multiple administrations of at least one inhibitor within a dosing period. Accordingly, in some embodiments, where administration of an agent that inhibits the Hh signalling pathway is by systemic, intraperitoneal, or intrapleural administration, the total aggregate dose per dosing period for an inhibitor ranges from about 0.5 mg/kg to about 25 mg/kg per total aggregate dose per dosing period, e.g., 0.6 mg/kg, 1 mg/kg, 2 mg/kg, 3 mg/kg, 4 mg/kg, 5 mg/kg, 8 mg/kg, 10 mg/kg, 12 mg/kg, 15 mg/kg, 18 mg/kg or another dose ranging from about 0.5 mg/kg to about 25 mg/kg per total aggregate dose. In some embodiments, the total aggregate dose per dosing period is about 1 mg/kg to about 10 mg/kg per total aggregate dose per dosing period.

In some preferred embodiments the at least one agent to inhibit the Hh signalling pathway is the small molecule inhibitor Vismodegib. In some embodiments, where administration of Vismodegib is systemic, the dose concentration in circulation is about 10 μM to about 80 μM, e.g., 15 μM, 20 μM, 25 μM, 30 μM, 35 μM, 40 μM, 45 μM, 50 μM, 60 μM, 70 μM, or another concentration in circulation from about 10 μM to about 80 μM. In some preferred embodiments, the dose concentration in circulation is at least about 20 μM to about 40 μM, e.g., 25 μM, 30 μM, 35 μM, or another concentration in circulation from at least about 20 μM to about 40 μM.

In some embodiments, where administration of Vismodegib is intralesional, the dose concentration is about 10 μM to about 40 μM per lesion, e.g., 15 μM, 20 μM, 25 μM, 30 μM, 35 μM per lesion, or another dose concentration from about 10 μM to about 40 μM. In other embodiments Vismodegib is administered intralesionally at a dose ranging from about 0.0025 mg/lesion to about 0.3 mg/lesion, e.g., 0.005 mg/lesion, 0.0075 mg/lesion, 0.01 mg/lesion, 0.02 mg/lesion, 0.025 mg/lesion, 0.04 mg/lesion, 0.05 mg/lesion, 0.07 mg/lesion, 0.1 mg/lesion, 0.15 mg/lesion, 0.2 mg/lesion, 0.25 mg/lesion, or another intralesional dose from about 0.0025 mg/lesion to about 0.3 mg/lesion. In preferred embodiments intralesional administration of Vismodegib is in a dose ranging from about 0.0025 mg/lesion to about 0.05 mg/lesion.

In some embodiments Vismodegib is administered by a systemic (e.g., oral), intraperitoneal, or intrapleural route at a dose of about 0.1 mg/kg to about 12 mg/kg per administration, e.g., 0.20 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 10 mg/kg, or another dose ranging from about 0.1 mg/kg to about 12 mg/kg. In some preferred embodiments, the dose of Vismodegib is about 2 mg/kg to about 5 mg/kg. In some preferred embodiments Vismodegib administered orally with a dose of about 150 mg to about 500 mg daily, e.g., 160 mg, 170 mg, 200 mg, 250 mg, 300 mg, 350 mg, 400 mg, or another oral dose from about 150 mg to about 500 mg daily.

In some embodiments, where a subject is to be treated for a disease amenable to intralesional administration (e.g., basal cell carcinoma or cutaneous warts), both an inhibitor of the Hh signalling pathway and a type II or type I interferon are administered by an intralesional route. In exemplary preferred embodiments a non-replicative recombinant adenovirus is used for expression of interferon gamma, and is administered in a dose ranging from about $5 \times 10^{10}$ viral particles/lesion to about $3 \times 10^{11}$ viral particles/lesion about 2 to 5 times per week, and a small molecule inhibitor of the Hh signalling pathway is administered orally in a dose ranging from about 2 mg/kg to about 5 mg/kg daily. In some embodiments the just-mentioned treatment is repeated for up to four weeks.

Pharmaceutical Compositions

Any of the therapeutic agents described herein can be formulated either alone or in combined pharmaceutical compositions as described herein for administration to a subject via any conventional means including, but not limited to, intralesional, parenteral (e.g., intravenous, subcutaneous, intramuscular, intraperitoneal, or intrapleural), oral, or transdermal administration routes.

Thus, in some embodiments provided herein is pharmaceutical composition for use in treatment of a disease characterised by aberrant cell proliferation, the pharmaceutical composition comprising: (i) at least one type II interferon and/or type I interferon, or a polynucleotide encoding a type II interferon and/or type I interferon; and (ii) at least one inhibitor of the Hedgehog (Hh) signalling pathway. In some embodiments the pharmaceutical composition also include an inhibitor of WNT signalling.

Also provided herein is a pharmaceutical composition for use in treatment of a disease characterised by aberrant cell proliferation, the pharmaceutical composition comprising: (i) at least one agent that increases activation of a receptor of at least one type II interferon and/or type I interferon; and (ii) at least one agent which inhibits the Hedgehog (Hh) signalling pathway. In some embodiments of the pharmaceutical (i) includes at least one type II interferon and/or type I interferon, or a polynucleotide encoding a type II interferon and/or type I interferon, or an agonist for a receptor of at least one type II interferon and/or type I interferon. In some embodiments the pharmaceutical composition includes a recombinant virus comprising the polynucleotide encoding the type II interferon and/or type I interferon for expression in a subject. In some preferred embodiments the interferon (or the interferon to be expressed) is interferon gamma.

Therapeutic agents can be formulated into any suitable dosage form, including but not limited to, injectable formulations, aqueous oral dispersions, liquids, mists, gels, syrups, elixirs, slurries, suspensions and the like, for oral ingestion by a patient to be treated, solid oral dosage forms, controlled release formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the therapeutic agents described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical solid dosage forms can include, in addition to the therapeutic agents, one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the therapeutic agents from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel® PH101, Avicel®PH102, Avicel®PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone®XL-10, and Povidone®K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

Liquid formulation dosage forms for oral administration can be aqueous suspensions selected from the group including, but not limited to, pharmaceutically acceptable aqueous oral dispersions, emulsions, solutions, elixirs, gels, and syrups.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, therapeutic agents described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the therapeutic agents in water-soluble form. Additionally, suspensions of the therapeutic agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of a therapeutic agent to allow for the preparation of highly concentrated solutions. Alternatively, the therapeutic agent may be in powder form for constitution with a suitable vehicle, e.g., sterile pyrogen-free water, before use. The therapeutic agents described herein may be in unit dosage forms suitable for single administration of precise dosages. In unit dosage form, the formulation is divided into unit doses containing appropriate quantities of one or more therapeutic agents. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Also provided herein are controlled release pharmaceutical compositions. Controlled release refers to the release of therapeutic agents from a dosage form in which they are incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of a therapeutic agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

The controlled release pharmaceutical compositions provided herein allow the release profile of an active agent within the combination formulation to be customised so that release of one or more of these active agents occurs over a preferred time interval. In some preferred embodiments, the agent that inhibits the Hh signalling pathway in the controlled release pharmaceutical composition is a small molecule inhibitor of Hh signalling pathway.

In some embodiments the pharmaceutical composition comprises from about 150 mg to about 3000 mg of a small molecule inhibitor of the Hh signalling pathway per day, e.g., 200 mg, 300 mg, 600 mg, 800 mg, 1000 mg, 1200 mg, 1600 mg, 1800 mg, 2000 mg, 2400 mg, 2800 mg, or another dose from about 100 mg to about 3000 mg of the small molecule inhibitor. In some embodiments the controlled release pharmaceutical composition comprises from about 200 mg to about 1400 mg of the small molecule inhibitor. In other embodiments the controlled release pharmaceutical composition comprises from about 600 mg to about 1000 mg of the small molecule inhibitor.

In some embodiments, one or more of the active agents is released over a time period ranging from about one hour to about five weeks, e.g., 2 hours, 3 hours, 4 hours, 6 hours, 8 hours, 12 hours, 18 hours, 24 hours, 2 days, 3 days, 5 days, 1 week, 10 days, 2 weeks, 18 days, 3 weeks, 4 weeks, or another period from about one hour to about five weeks.

In some embodiments, the controlled release profile has a release rate higher at the beginning of the release period following administration, and then decreases over time (first order release kinetics). In other embodiments, the release rate progressively increases over the release period following administration. In preferred embodiments, the release profile remains relatively constant over the entire release period following administration until all of the active agent is released (zero order release kinetics).

In preferred embodiments the release profile of a small molecule inhibitor of the Hh signalling pathway upon administration of the controlled release pharmaceutical composition is adapted to avoid induction of at least one adverse event in the human subject. In some embodiments, the release rate of a small molecule inhibitor of the Hh signalling pathway is about 0.5% of the total dose/day to about 10% of the total dose per day, e.g., 0.6%, 0.8%, 1%, 1.1%, 1.2%, 1.5%, 1.8%, 2%, 2.5%, 2.75%, 3%, 3.5%, 4%, 6%, 7%, 8%, 9% or another percentage of the total dose per day from about 0.5% to about 10% per day.

In some embodiments, the rate of release (as a percentage of total dose) of a small molecule inhibitor in the controlled release formulation is distinct from that the release profile of another active agent in the formulation (e.g., a recombinant virus, a polynucleotide, or a purified protein or peptide).

In some embodiments, where the controlled release pharmaceutical composition includes interferon gamma, the interferon gamma is released at a rate of about 1 µg/day to about 10 µg/day for systemic delivery, e.g., 2 µg/day, 3 µg/day, 4 µg/day, 5 µg/day, 7 µg/day, 8 µg/day, or another release rate for systemic administration of purified interferon gamma ranging from about 1 µg/day to about 10 µg/day.

In some embodiments, where the controlled release pharmaceutical composition includes interferon gamma, the interferon gamma is released at a rate of about 5 ng/day to about 200 ng/day for localized delivery, e.g., implantation within a tumour, e.g., 10 ng/day, 20 ng/day, 30 ng/day, 50 ng/day, 75 ng/day, 100 ng/day, 125 ng/day, 150 ng/day, 175 ng/day, or another release rate for local administration ranging from about 10 ng/day to about 200 ng/day.

Where at least one recombinant virus is to be included in a pharmaceutical composition described herein, such pharmaceutical compositions described herein may comprise a range of viral titers, expressed as a 50% tissue culture infective dose ($TCID_{50}$)/ml and/or viral particles (vp)/ml, depending on a number of considerations including the condition to be treated, the subject to be treated, a desired release rate and the desired treatment period per dose. In some embodiments the pharmaceutical compositions described herein have a titer of about $1\times10^9$ $TCID_{50}$/ml to about $3\times10^{10}$ $TCID_{50}$/ml, e.g., $1.5\times10^9$ $TCID_{50}$/ml, $1.8\times10^9$ $TCID_{50}$/ml, $2.0\times10^9$ $TCID_{50}$/ml, $3.0\times10^9$ $TCID_{50}$/ml, $4.0\times10^9$ $TCID_{50}$/ml, $5.0\times10^9$ $TCID_{50}$/ml, $5.5\times10^9$ $TCID_{50}$/ml, $6.0\times10^9$ $TCID_{50}$/ml, $6.5\times10^9$ $TCID_{50}$/ml, $7.0\times10^9$ $TCID_{50}$/ml, $7.5\times10^9$ $TCID_{50}$/ml, $8.0\times10^9$ $TCID_{50}$/ml, $8.5\times10^9$ $TCID_{50}$/ml, $9.0\times10^9$ $TCID_{50}$/ml, $1.0\times10^{10}$ $TCID_{50}$/ml, $1.5\times10^{10}$ $TCID_{50}$/ml, $2.0\times10^{10}$ $TCID_{50}$/ml, $2.5\times10^{10}$ $TCID_{50}$/ml, or another $TCID_{50}$/ml value from about $1\times10^9$ $TCID_{50}$/ml to about $3\times10^{10}$ $TCID_{50}$/ml. In some preferred embodiments, the $TCID_{50}$/ml is about $4\times10^9$ $TCID_{50}$/ml to $8\times10^9$ $TCID_{50}$/ml.

In some embodiments the equivalence of vp/$TCID_{50}$ is approximately 20 to 100 vp/$TCID_{50}$. Accordingly, in some embodiments the pharmaceutical compositions described herein have a titer of about $2\times10^{10}$ vp/ml to about $3\times10^{12}$ vp/ml, e.g., $2\times10^{10}$ vp/ml, $3\times10^{10}$ vp/ml, $4\times10^{10}$ vp/ml, $5\times10^{10}$ vp/ml, $6\times10^{10}$ vp/ml, $7\times10^{10}$ vp/ml, $8\times10^{10}$ vp/ml, $9\times10^{10}$ vp/ml $1\times10^{11}$ vp/ml, $2\times10^{11}$ vp/ml, $3\times10^{11}$ vp/ml, $4\times10^{11}$ vp/ml, $5\times10^{11}$ vp/ml, $6\times10^{11}$ vp/ml, $7\times10^{11}$ $8\times10^{11}$ vp/ml, $9\times10^{11}$ vp/ml, $1\times10^{12}$ vp/ml, $2\times10^{12}$ vp/ml, or another titer from about $2\times10^{10}$ vp/ml to about $3\times10^{12}$ vp/ml. In some preferred embodiments the titer is from about $3\times10^{10}$ vp/ml to about $8\times10^{11}$ vp/ml. In other preferred embodiments the titer of the pharmaceutical composition is about $3\times10^{10}$ viral particles/ml to about $5\times10^{12}$ viral particles/ml.

Suitable controlled release matrices for controlled release pharmaceutical compositions have been described in art. In some embodiments, the $SiO_2$ matrix hydrogel is a bioresorbable sol-gel derived Tetraethyl orthosilicate (AKA "tetrathoxysilane" or "TEOS") Si $(OC_2H_5)_4$ matrix gel ("$SiO_2$ matrix gel"). This technology has been commercialised by DelSiTech Ltd (Turku, Finland). Such a bioresorbable $SiO_2$ matrix gel is useful for sustained delivery of active therapeutic agents including small molecule drugs and recombinant viruses as described in international patent application publications WO2005082781 entitled "Method for Preparing Adjustably Bioresorbable Sol-Gel Derived $SiO_2$" and WO2007135224 entitled "Method for Storing Silica-Based Material, Package Produced with the Method, and Use of Package for Packaging of Silica-Based Products." This technology has been commercialised by DelSiTech Ltd (Turku, Finland).

In brief, the $SiO_2$ matrix gel sol-gel is prepared by the sol-gel process wherein the $SiO_2$ matrix gel is prepared from a sol comprising $SiO_2$ that has turned to a gel. Sol-gel derived $SiO_2$ is typically prepared from alkoxides or inorganic silicates that via hydrolysis form a sol that contains either partly hydrolysed silica species or fully hydrolysed silicic acid. Consequent condensation reactions of SiOH containing species lead to formation of larger silica species with increasing amount of siloxane bonds. Furthermore, the species aggregate, form nanosized particles and/or larger aggregates until a gel is formed. In the form of a gel, the solid state dominates, but the system still contains varying amounts of liquids and the material is typically soft and viscoelastic before drying and hard and brittle if it is extensively dried. In the form of a sol, liquid state dominates, but the system contains varying amounts of solid phase(s) and the material is still flowable. The time from when the $SiO_2$ sol is prepared until the sol turns to a gel is referred to as sol ageing time. Spontaneous drying typically occurs when the sol is aged so that the system allows evaporation in ambient conditions. Generation of the controlled release pharmaceutical composition is achieved by adding to the sol, before gel formation, the desired amounts of the active therapeutic agents to be included in the pharmaceutical composition (e.g., recombinant virus expressing interferon gamma and a small molecule inhibitor of the Hh signalling pathway). As an end result of this process, a pharmaceutical composition is obtained which contains a $SiO_2$ matrix hydrogel that contains one or more recombinant viruses for expression of a Type I or Type II interferon; an agent for inhibiting the Hh signalling pathway; $SiO_2$ matrix hydrogel; and silica microparticles, where the recombinant viruses and the agent for inhibiting the Hh signalling pathway are interspersed within the $SiO_2$ matrix hydrogel.

Release rates of the active agents in $SiO_2$ gel-based controlled release pharmaceutical compositions can be adjusted as needed. Generally the maximum dissolution rate of the $SiO_2$ gel matrix and release rate of the active agents occurs for $SiO_2$ gels having a molar ratio of water to alkoxide of about 2, with ratios lower or higher than this resulting in slower dissolution and release rates. Further, It should also be noted that large amounts of active agent comprised within the $SiO_2$ gel matrix increases dissolution of the matrix and the release rate(s) of the active agents.

The controlled release pharmaceutical compositions can be prepared as nano- and microspheres mainly for oral, parenteral, pulmonary, topical, transdermal and surgically implantable administration.

In some embodiments the rate of recombinant virus release (rate of dissolution) observed for a pharmaceutical composition described herein occurs at approximately ten times the rate in vitro than it does in vivo.

In exemplary, non-limiting embodiments, the pH of a water and tetraethyl orthosilicate (TEOS) mixture at an initial molar ratio of about 100:1 to 150:1 is adjusted to pH 2 with hydrochloric acid and vigorously stirred at room temperature for 25 min. The pH of the sol is then adjusted to the desired pH (6, 6.5 or 7) by adding 0.1 M NaOH. The sol is cooled in an ice-water bath and the desired amounts of the active agents to be included are added.

In some embodiments the $SiO_2$ matrix hydrogel in the pharmaceutical composition comprise water and TEOS in a final molar ratio of about 5:1 to about 4,000:1, e.g., 10:1, 25:1, 50:1, 75:1, 100:1, 150:1, 200:1, 300:1, 400:1, 500:1, 750:1, 1,000:1, 2,000:1, 3,000:1, or another final molar ratio of water to TEOS from about 50:1 to about 700:1, or about 5:1 to about 1,000:1. In some preferred embodiments the final molar ratio of water to TEOS is about 400:1.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments a pharmaceutical composition described herein is generated as a depot formulation.

EXAMPLES

Example 1—Anti-Tumour Efficacy of a Combination Therapy of Adenovirus Expressing IFNγ and Vismodegib Vismodegib is a hedgehog inhibitor approved for use in BCC. The anti-tumour efficacy of the combination of Ad5-mIFNgamma with Vismodegib will be evaluated in a number of murine tumour models. Suitable models include the murine melanoma cell line, B16-F0 and later in subcutaneous tumour graft models 4T1 (breast tumour line), CT26 (mouse colon carcinoma line) and human tumour xenograft MDA-MB-231 (human breast cancer line).

Experimental Design $2 \times 10^5$ tumour cells will be implanted subcutaneously in C57BL/6 mice to generate tumours. Once tumours are 3-6 mm in diameter, $1 \times 10^{10}$ viral particles (VPs)/tumour of Ad-5-mIFNγ, Vismodegib (50 mg or 100 mg/kg by oral gavage), or both will be administered to various experimental groups according to the schedule shown in Table 1. In Table 1, day "0" denotes the initial day of treatment. Vismodegib will be administered in DMSO or PEG 400/5% dextrose in water (75:25 v/v).

Mice to be monitored by caliper measurement for tumour growth every other day and survival. End points will be determined according to approved animal ethics requirements including maximum tumour size allowed and animal sacrifice if any signs of distress are apparent.

Data Analysis

Data will be recorded and represented in individual tumour growth curves of all animals in groups as mean±error as well as statistical significance. Survival will be plotted as Kaplan-Meier survival curves and statistical comparison will be performed using a log-rank test.

Tumours from 2 mice/group (point of removal to be determined) from above for mRNA isolation, formalin fixation and/or multiparameter flow cytometric analysis of tumour infiltrating cells.

TABLE 1

Treatment Schedule for Administration of Ad-5-mIFN-gamma and Vismodegib Combination Treatment in a Murine Tumour Model

| | | Agent (Ad-mIFNγ) | | | Agent (Vismodegib) | | | |
|---|---|---|---|---|---|---|---|---|
| Group | N | Dose | Schedule (Day) | Route | Dose | Schedule (Day) | Route | Comment |
| 1 | 10 | Vehicle | 0, 1, 2 | IT | Vehicle | 0-6 | Oral | Tumour response and survival |
| 2 | 10 | Vehicle | 0, 1, 2 | IT | 50 mg/kg | 0-6 | Oral | will be evaluated before end |
| 3 | 10 | $10^{10}$ VP | 0, 1, 2 | IT | Vehicle | 0-6 | Oral | of $1^{st}$ treatment cycle and |
| 4 | 10 | $10^{10}$ VP | 0, 1, 2 | IT | 50 mg/kg | 0-6 | Oral | will assess if another course of treatment will be initiated (D7, 8, 9 Ad-mIFNγ and Vismo D7-D13) |
| 5 | 10 | Vehicle | 0, 7, 14 | IT | Vehicle | 3x/weekx3 | Oral | |
| 6 | 10 | Vehicle | 0, 7, 14 | IT | 100 mg/kg | 3x/weekx3 | Oral | |
| 7 | 10 | $10^{10}$ VP | 0, 7, 14 | IT | Vehicle | 3x/weekx3 | Oral | |
| 8 | 10 | $10^{10}$ VP | 0, 7, 14 | IT | 100 mg/kg | 3x/weekx3 | Oral | |

Example 2—Combination Therapy of Adenovirus Expressing IFNγ and Vismodegib Reduces Tumour Growth in Mice Methods Mice Female B6D2F1/J mice (Jackson Laboratories) were ten weeks old and had an individual body weight (BW) range of 19.4 to 29.9 g on Day 1 of the study.

Tumour Cell Culture

The B16F10 murine colon carcinoma cell line was maintained in DMEM medium containing 10% fetal bovine serum, 2 mM glutamine, 100 units/mL sodium penicillin G, 25 μg/mL gentamicin, and 100 μg/mL streptomycin sulfate. The tumour cells were cultured in tissue culture flasks in a humidified incubator at 37° C., in an atmosphere of 5% $CO_2$ and 95% air.

In Vivo Tumour Implantation and Measurement

B16F10 cells were harvested during log phase growth and resuspended in PBS. Each mouse was injected subcutaneously in the right flank with $5\times10^5$ cells (in a 0.1 mL cell suspension). Tumours were calipered in two dimensions to monitor growth as their mean volume approached the desired 30 to 60 mm$^3$ range. Tumour size, in mm$^3$, was calculated from:

$$\text{Tumour Volume} = \frac{w^2 \times l}{2}$$

where w=width and l=length, in mm, of the tumour. Tumour weight can be estimated based on the assumption that 1 mg is equivalent to 1 mm$^3$ of tumour volume.

Eight days after tumour cell implantation, on Day 1 of the study, animals were sorted into eight groups (n=10 per group) according to tumour volume, with individual tumour volumes ranging from 32 to 63 mm$^3$ and group mean tumour volumes ranging from 41 to 42 mm$^3$. Tumour progression was monitored using caliper measurements three times weekly for the duration of the study.

Therapeutic Agents

Vismodegib and Ad5-mIFNg (stock concentration $3.3\times10^{12}$ viral particles/mL) were stored at −80° C. prior to formulation. On each day of dosing, Vismodegib was dissolved in vehicle 2 (75% PEG400:25% D5W (5% dextrose in water)) to obtain 5 mg/mL and 10 mg/mL dosing solutions which delivered a dose of 50 mg/kg and 100 mg/kg when administered in a volume of 10 mL/kg (0.2 mL per 20 g mouse), adjusted to the body weight of each animal.

On the first day of dosing, Ad5-mIFNg was thawed rapidly and diluted in vehicle 1 (1 M saccharose, 54 mg/L Tween® 80, 10 mM Tris, 1 mM $MgCl_2$, 150 mM NaCl, pH 8) to obtain dosing solutions of $5\times10^{11}$ particles/mL and $2\times10^{11}$ particles/mL, which delivered $1\times10^{10}$ particles/animal when dosed in a fixed volume of 20 μL and 50 μL per animal, respectively.

Treatment

On Day 1 of the study, female mice bearing established B16F10 tumours were sorted into eight groups (n=10 per group) and began dosing according to the treatment plan summarized in Table 2. Vehicle 1 and Ad5-mIFNg ($1\times10^{10}$ particles per animal) were administered intratumourally (itu) in a fixed volume of either 20 μL or 50 μL; vehicle 2 and Vismodegib were administered orally (po) in a volume of 10 mL/kg (0.2 mL per 20 g mouse), adjusted to the body weight of each animal. The groups were as follow:

Group 1 served as the control group and received 20 μL vehicle 1 itu once a day (qd) for three days (qdx3) and vehicle 2 po qdx7.

Group 2 received 20 μL vehicle 1 itu qdx3 and 50 mg/kg vismodegib po qdx7.

Group 3 received $1\times10^{10}$ particles/animal Ad5-mIFNg in 20 μL itu qdx3 and vehicle 2.

Group 4 received $1\times10^{10}$ particles/animal Ad5-mIFNg 1 itu qdx3 and 50 mg/kg vismodegib 2 po qdx7.

Group 5 received 20 μL vehicle 1 itu once a week for a week (qwkx1) followed by 50 μL vehicle 1 itu qwkx1 (starting on Day 8) in addition to vehicle 2 po three times a week (tiwk) to Day 10.

Group 6 received 20 μL vehicle 1 itu once a week for a week (qwkx1) followed by 50 μL vehicle 1 itu qwkx1 (starting on Day 8) and 100 mg/kg Vismodegib in vehicle 2 po tiwk to Day 13.

Group 7 received 20 μL containing $1\times10^{10}$ particles/animal Ad5-mIFNg itu once a week for a week (qwkx1) followed by 50 μL containing $1\times10^{10}$ particles/animal Ad5mIFNg itu qwkx2 (starting on Day 8) and vehicle 2 three times a week for three weeks (tiwkx3).

Group 8 received 20 μL containing $1\times10^{10}$ particles/animal Ad5-mIFNg itu once a week for a week (qwkx1) followed by 50 μL containing $1\times10^{10}$ particles/animal Ad5mIFNg itu qwk×2 (starting on Day 8) and 100 mg/kg vismodegib po three times a week for three weeks (tiwk×3).

Endpoint and Tumour Growth Delay (TGD) Analysis

Tumours were measured using calipers three times per week, and each animal was euthanized when its tumour reached the pre-determined tumour volume endpoint of 1500 mm$^3$ or on the last day of the study (Day 45). Animals that exited the study for tumour volume endpoint were documented as euthanized for tumour progression (TP), with the date of euthanasia.

Results

B16F10 tumour-bearing mice were treated as indicated in Table 2 and tumour growth monitored by caliper measurement. As shown in FIG. 1, treatment with oral Vismodegib qdx7 (G2) or tiwkx3 (G6) did not significantly reduce tumour growth in mice compared to the control vehicle treated groups. In fact, none of the mice in these groups were alive after day 12 (culled at ethical end point). For comparison of tumour inhibition, mean tumour volumes were compared when there were at least four mice alive out of an initial eight mice/group.

Ad5-mIFNg administered intratumourally either qdx3 (G3) or qwkx1 (G7) significantly inhibited tumour growth compared to controls (G1 and G6). There was no significant difference in therapeutic efficacy in the combination of treatment dose regimen Ad5-mIFNg (qwkx1) alone and vehicle 2 (G7) versus Ad5-mIFNg (qwkx1) in combination with Vismodegib (tiwkx3) (G8). In contrast, a combination treatment dosing of Ad5-mIFNg (qdx3) and Vismodegib (qdx7) (G4) retarded the tumour growth more than the individual treatments (G3 and G2). On day 36, 50% of the mice (4 out of 8 mice) in G4 were still alive compared to 1 out of 8 mice treated with Ad5-mIFNg only qdx3 (G3) or no mice from the group treated with Vismodegib only (G2) qdx7. On day 20 the mean tumour size of the (G4) combination treatment group was 30% that of the tumours of mice treated with Ad5-mIFNg alone (G3).

sporadic or basal cell nevus syndrome patients received Vismodegib (150 mg, oral) daily for four weeks and three single intralesional injections of ASN-002 of 1×10" VP/lesion (one injection per week at weeks 3-5). Patients were monitored for treatment response through week 26 of the study (i.e., post-treatment period of 19 weeks).

Over this period a total of 23 lesions was monitored (including single or multiply injected lesions, and non-injected lesions). At week 25, a loco-regional complete histological clearance (CHC) of >50% was observed in response to this combination treatment. In comparison a previous study using ASN-002 treatment alone, loco-regional CHC of 0% was observed at week 18. In a study by Sofen et al. (2015), operable basal cell carcinoma patients receiving a daily dose of 150 mg of Vismodegib over a period of 12 weeks exhibited a loco-regional CHC of 16%.

Thus, as expected based on the methods disclosed herein, the results of this ongoing study to date underscore that combination treatment with Vismodegib and ASN-002 provides a superior therapeutic response compared to monotherapy with either of these therapeutic agents.

The present application claims priority from AU2020900585 filed 28 Feb. 2020, and AU 2020900813 filed 17 Mar. 2020, the entire contents of both of which are incorporated herein by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present

TABLE 2

Protocol Design for the B16F10-e357 Study

| | Treatment Regimen 1 | | | | Treatment Regimen 2 | | | | Treatment Regimen 3 | | | |
|---|---|---|---|---|---|---|---|---|---|---|---|---|
| Group | Agent | u/animal | Route | Schedule | Agent | u/animal | Route | Schedule | Agent | u/animal | Route | Schedule |
| 1 | Vehicle 1 | — | itu | qd × 3 | Vehicle 2 | — | po | qd × 7 | — | — | — | — |
| 2 | Vehicle 1 | — | itu | qd × 3 | Vismodegib | 50$^a$ | po | qd × 7 | — | — | — | — |
| 3 | Ad5-mIFNg | 1 × 10$^{10}$ | itu | qd × 3 | Vehicle 2 | — | po | qd × 7 | — | — | — | — |
| 4 | Ad5-mIFNg | 1 × 10$^{10}$ | itu | qd × 3 | Vismodegib | 50$^a$ | po | qd × 7 | — | — | — | — |
| 5 | Vehicle 1 | — | itu | qwk × 1 | Vehicle 1 | — | itu | qwk × 2 (start on Day 8) | Vehicle 2 | — | po | tiwk × 3 |
| 6 | Vehicle 1 | — | itu | qwk × 1 | Vehicle 1 | — | itu | qwk × 2 (start on Day 8) | Vismodegib | 100$^a$ | po | tiwk × 3 |
| 7 | Ad5-mIFNg | 1 × 10$^{10}$ | itu | qwk × 1 | Ad5-mIFNg | 1 × 10$^{10}$ | itu | qwk × 2 (start on Day 8) | Vehicle 2 | — | po | tiwk × 3 |
| 8 | Ad5-mIFNg | 1 × 10$^{10}$ | itu | qwk × 1 | Ad5-mIFNg | 1 × 10$^{10}$ | itu | qwk × 2 (start on Day 8) | Vismodegib | 100$^a$ | po | tiwk × 3 |

Table 2 displays the study design as of Day 1 of the study
Vehicle 1 = Vehicle for Ad5-mIFNg-ASCND Saccharose 1M, Tween80 54 mg/l, Tris 10 mM, MgCl$_2$ 1 mM, NaCl 150 mM, pH 8
Vehicle 2 = Vehicle for Vismodegib- ASCND PEG 400/5% dextrose in water (75:25 v/v)
$^a$mg/kg Example 3—Combination Therapy of Adenovirus Expressing IFNγ and Vismodegib in Basal Cell Nevus Syndrome Patients In an ongoing clinical trial (26 week duration), patients presenting with multiple low risk basal cell carcinomas in specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Amer et al. (2014) Molecular and Cellular Therapies 2, 27.
Boohaker et al (2018) Cancer Lett., 434:11-21.
Bucholz et al. (2015) Trends in Biotechnology 33(12), 777-790.
Cattaneo (2010) PLoS Pathogens 6(6), e10010973.
Chang et al. (2010) Journal of Urology 183(4), 1611-1618.
Chang et al. (2015) Angew. Chem. Int. Ed., 54:11760-11764.
Chi et al. (2012) Cell Signal, 24(6):1222-1228.
Choi et al. (2019) J Immunother. Cancer, 7:304.
Clinical Trial NCT02550678; ASN-002/SP-002. A Phase I/IIa Study of the Efficacy and Safety of ASN-002/SP-002 in Adult Patients with Low Risk Nodular Basal Cell Carcinoma: Ascend Biopharmaceuticals Ltd; 2019.
Cody et al. (2013) Journal of Genetic Syndromes & Gene Therapy 4(1), 126.
Coon et al. (2010) Molecular Cancer Therapy, 9:2627-2636.
Dahlen et al. (2018) Ther. Adv. Vaccines Immunother., 6:3-17.
Diao et al. (2018) Molecular Oncology, 12:1718-1734.
Emeagi et al. (2013) Current Molecular Medicine 13(4), 602-625.
Finke et al. (2005) Current Topics in Microbiology and Immunology 292, 165-200.
Fukazawa et al. (2010) International Journal of Molecular Medicine, 25:3-10.
Gao et al. (2006) Gene Therapy, 13(22):1587-1594.
Gene Therapy Protocols Methods in Mol. Biol., Vol. 2 Joseph LeDoux (ed.), 2008.
Gene Therapy Protocols Methods in Mol. Biol., Vol. 1 Joseph LeDoux (ed.), 2008.
Guo et al. (2002) Blood 99, 3419-3426.
Hegde et al. (2012) International Journal of Cancer, 131 (12):2951-2960.
Herpes Simplex Virus: Methods and Protocols, Methods in Mol. Biol., Diefenbach and Fraefel (eds), 2014.
Hoang-Le et al. (2009) Gene Therapy 16, 190-199.
Lear et al. (1997) Postgraduate Medical Journal, 73(863): 538-542.
Li et al. (2018) Cancer Immunol. Res., 6:178-188.
Li et al. (2019) Acta Pharmacologica Sinica, 40(2):257-267.
Liu et al. (2015) Current Drug Metabolism, 16(2):152-165.
Lundstrom (2015) Viruses 7(5), 2321-2333.
Martinez-Sales (1999) Current Opinion in Biotechnology 10, 458-464.
Merten et al. (2016) Molecular Therapy—Methods & Clinical Development 3, 16017.
Morizono et al. (2005) Nature Medicine 11, 346-352.
Münch et al. (2011) Molecular Therapy 19, 686-693.
Münch et al. (2013) Molecular Therapy 21, 109-118.
Nakamura et al. (2007) Anticancer Research, 27:3743-3748.
Narita et al. (2008) Clinical Cancer Research, 14(18):5769-5777.
Owens et al. (2017) Journal of the American Chemical Society, 139(36):12559-12568.
Quetglas et al. (2010) Virus Research 153(2), 179-196.
Sasikumar et al. (2013) J. Immunother. Cancer, 1:024.
Sasikumar et al. (2019) Cancer Therapy Mol. Cancer Ther., 18:1081-1091.
Sekulic et al. (2012) The New England Journal of Medicine, 366:2171-2179.
Singh et al. (2009) Human Genetics, 125(1):95-103.
Sofen et al. (2015) Journal of Academic Dermatology 73:99-105.
Stone et al. (1999) Journal of Cell Science, 112, Pt(23): 4437-4448.
Tang et al. (2012) The New England Journal of Medicine, 366(23):2180-2188.
Tang et al. (2016) Lancet Oncology, 17(12):1720-1731.
Trichas et al. (2008) BMC Biology 6, 40.
Usme-Ciro et al. (2013) Virology Journal 10, 185.
Wu et al. (2018) Stem Cell Research, 27:5-9.
Yoo et al. (2019) Sci. Rep., 9:4712.
Youn et al. (2015) Expert Opinion on Biological Therapy, 15: 1337-134.

---

SEQUENCE LISTING

```
<160> NUMBER OF SEQ ID NOS: 1

<210> SEQ ID NO 1
<211> LENGTH: 27
<212> TYPE: PRT
<213> ORGANISM: Artificial Sequence
<220> FEATURE:
<223> OTHER INFORMATION: Peptide derived from Hedgehog-Interacting
      Protein
<220> FEATURE:
<221> NAME/KEY: Macrocycle
<222> LOCATION: (18)..(24)
<223> OTHER INFORMATION: O-(2-bromoethyl)-tyrosine macrocyclic link to
      cysteine 24

<400> SEQUENCE: 1

Met Asp Tyr Lys Asp Asp Asp Lys Gly Ser Gly Ser Thr Leu Ser
1               5                   10                  15

Trp Tyr Glu Ala Met Asp Met Cys Thr Asp Thr
            20                  25
```

---

Hoffmann et al. (2018) Scientific Reports, 8(1):12538.
Hsiao et al. (2018) Journal of Cell Science, 131(24).
Konermann et al. (2018) Cell, 173(3):665-676.
Lacouture et al. (2018) The Oncologist, 21(10):1218-1229.
Laner-Plamberger et al. (2013) PLoS One, 8(9):e75317.

The invention claimed is:
1. A method of treating a human subject suffering from basal cell carcinoma (BCC), the method comprising administering to the human subject a therapeutically effective amount of: (i) a recombinant DNA virus for expression of interferon gamma by intralesional or perilesional injection into one or more BCC-related lesions; and (ii) Vismodegib or Sonidegib, wherein the subject is treated over a period of one week to twelve weeks.

2. The method of claim 1, wherein the recombinant DNA virus is an adenovirus.

3. The method of claim 1, comprising administering at least $5 \times 10^{10}$ viral particles (vp) per lesion.

4. The method of claim 3, comprising administering from $5 \times 10^{10}$ vp per lesion to $1.5 \times 10^{11}$ vp per lesion.

5. The method of claim 1, comprising administration of Sonidegib.

6. The method of claim 1, comprising administration of Vismodegib.

7. The method of claim 1, wherein the Vismodegib or Sonidegib is administered at a dose of 50 mg/day to 500 mg/day.

8. The method of claim 7, wherein the dose is 150 mg/day.

9. The method of claim 1, wherein the Vismodegib or Sonidegib is administered systemically.

10. The method of claim 9, wherein the Vismodegib or Sonidegib is administered orally.

\* \* \* \* \*